United States Patent
Elliot et al.

(10) Patent No.: US 10,011,015 B2
(45) Date of Patent: Jul. 3, 2018

(54) BIOLOGICAL REACTION APPARATUS WITH DRAINING MECHANISM

(71) Applicant: LEICA BIOSYSTEMS MELBOURNE PTY LTD, Mount Waverly, Victoria (AU)

(72) Inventors: Stuart Elliot, Glen Iris (AU); Andrew McLellan, Surrey Hills (AU); Chester Henderson, Mount Waverly (AU); Mark Dockrill, Chadstone (AU); Simon Harris, Ashburton (AU); Peter Riddell, Rowville (AU)

(73) Assignee: LEICA BIOSYSTEMS MELBOURNE PTY LTD, Mount Waverly, Victoria (AU)

( * ) Notice: Subject to any disclaimer, the term of this patent is extended or adjusted under 35 U.S.C. 154(b) by 0 days.

(21) Appl. No.: 13/714,616

(22) Filed: Dec. 14, 2012

(65) Prior Publication Data

US 2013/0123979 A1 May 16, 2013

Related U.S. Application Data

(60) Continuation of application No. 12/697,684, filed on Feb. 1, 2010, now Pat. No. 9,029,154, which is a
(Continued)

(30) Foreign Application Priority Data

Jun. 20, 2002 (AU) .................................... PS3114/02
Mar. 31, 2003 (AU) ................................ 2003901871

(51) Int. Cl.
*G01N 21/00* (2006.01)
*B01L 3/00* (2006.01)
(Continued)

(52) U.S. Cl.
CPC ............. *B25J 9/1679* (2013.01); *B01L 3/545* (2013.01); *B01L 9/523* (2013.01);
(Continued)

(58) Field of Classification Search
CPC ..... G01N 2035/00138; G01N 35/0099; G01N 1/34; G01N 2021/0378;
(Continued)

(56) References Cited

U.S. PATENT DOCUMENTS 4,678,752 A 7/1987 Thorne
4,731,335 A 3/1988 Brigati
(Continued)

FOREIGN PATENT DOCUMENTS

EP 0 485 816 5/1992
EP 1 118 379 A2 7/2001
(Continued)

OTHER PUBLICATIONS

International Search Report for PCT/AU2003/000779, dated Sep. 26, 2003.
(Continued)

*Primary Examiner* — Dean Kwak
(74) *Attorney, Agent, or Firm* — Sughrue Mion, PLLC

(57) ABSTRACT

A biological reaction apparatus for receiving at least one substrate having a sample located in a sample region, and a separate cover, such that a reaction chamber is formed between the cover and substrate over the sample region, wherein the apparatus includes a locating means to locate the substrate; a cover locating means for locating and moving the cover with respect to the substrate; a fluid dispensing means for dispensing fluid into the reaction chamber; and a draining mechanism; wherein the draining mechanism includes wicking means.

21 Claims, 16 Drawing Sheets

Related U.S. Application Data division of application No. 12/560,850, filed on Sep. 16, 2009, now abandoned, which is a continuation of application No. 10/518,626, filed as application No. PCT/AU03/00779 on Jun. 20, 2003, now abandoned.

(51) Int. Cl.
  *G01N 31/22* (2006.01)
  *G01N 35/00* (2006.01)
  *B25J 9/16* (2006.01)
  *B01L 9/00* (2006.01)
  *G02B 21/34* (2006.01)
  *G01N 35/10* (2006.01)

(52) U.S. Cl.
  CPC ....... *G01N 35/00029* (2013.01); *G02B 21/34* (2013.01); *G01N 2035/00079* (2013.01); *G01N 2035/00138* (2013.01); *G01N 2035/00752* (2013.01); *G01N 2035/1025* (2013.01); *Y10T 29/49826* (2015.01); *Y10T 436/10* (2015.01); *Y10T 436/108331* (2015.01)

(58) Field of Classification Search
  CPC ... G01N 2035/00079; G01N 35/00029; G01N 1/36; G01N 2035/00089; G02B 21/34; B01L 2200/142; B01L 2300/0838; B01L 2400/0481; B01L 3/021; B01L 3/0293; B01L 3/545; B01L 7/52; B01L 9/06; B01L 9/523; B01L 2200/025; B01L 2300/0822; B01L 9/52; B01L 2200/10
  USPC ....... 422/50, 300, 400, 401, 430, 62, 63, 65, 422/68.1, 500, 547, 551; 436/43, 47
  See application file for complete search history.

(56) References Cited

U.S. PATENT DOCUMENTS

| | | | |
|---|---|---|---|
| 4,790,640 A | 12/1988 | Nason | |
| 4,985,206 A | 1/1991 | Bowman et al. | |
| 5,023,187 A | 6/1991 | Koebler et al. | |
| 5,225,325 A | 7/1993 | Miller et al. | |
| 5,250,262 A * | 10/1993 | Heidt | G01N 35/00029 422/63 |
| 5,281,516 A * | 1/1994 | Stapleton | B01L 7/52 165/61 |
| 5,439,649 A * | 8/1995 | Tseung | B01L 3/0275 118/300 |
| 5,573,727 A | 11/1996 | Keefe | |
| 5,595,707 A | 1/1997 | Copeland et al. | |
| 5,609,822 A | 3/1997 | Carey et al. | |
| 5,706,038 A | 1/1998 | Jackson et al. | |
| 5,804,141 A | 9/1998 | Chianese | |
| 5,985,669 A | 11/1999 | Palander | |
| 6,070,476 A | 6/2000 | Shine et al. | |
| 6,180,061 B1 | 1/2001 | Bogen et al. | |
| 6,337,490 B1 | 1/2002 | Furusato et al. | |
| 6,349,264 B1 | 2/2002 | Rhett et al. | |
| 6,352,861 B1 * | 3/2002 | Copeland | B01F 5/0057 141/130 |
| 6,395,536 B2 * | 5/2002 | Freeman | B01L 7/52 435/286.5 |
| 6,495,106 B1 * | 12/2002 | Kalra | G01N 1/312 118/120 |
| 6,673,620 B1 | 1/2004 | Loeffler et al. | |
| 6,810,921 B2 | 11/2004 | Schosser | |
| 7,223,363 B2 * | 5/2007 | McNeely | B01F 5/10 422/417 |
| 7,303,725 B2 * | 12/2007 | Reinhardt | B01L 9/52 422/63 |
| 2002/0072122 A1 | 6/2002 | Copeland et al. | |
| 2002/0090730 A1 | 7/2002 | Eckert et al. | |
| 2003/0077329 A1 | 4/2003 | Kipp et al. | |
| 2004/0053302 A1 | 3/2004 | Livak et al. | |
| 2004/0086428 A1 * | 5/2004 | Loeffler et al. | 422/100 |
| 2004/0120855 A1 | 6/2004 | Reichel et al. | |
| 2005/0186114 A1 * | 8/2005 | Reinhardt | B01L 9/52 422/65 |
| 2006/0148063 A1 * | 7/2006 | Fauzzi | G01N 1/31 435/286.4 |
| 2006/0153736 A1 * | 7/2006 | Kalra | B01L 3/508 422/400 |

FOREIGN PATENT DOCUMENTS

| | | |
|---|---|---|
| EP | 1 174 702 | 1/2002 |
| JP | 62-98231 A | 5/1987 |
| JP | 62-119460 A | 5/1987 |
| JP | 2-76227 A | 3/1990 |
| JP | 5-166714 A | 7/1993 |
| JP | 5-504627 A | 7/1993 |
| JP | 8-129014 A | 5/1996 |
| JP | 8-207296 A | 8/1996 |
| JP | 10-512048 A | 11/1998 |
| JP | 2001-41954 A | 2/2001 |
| JP | 2001-183269 A | 7/2001 |
| JP | 2001-296219 A | 10/2001 |
| JP | 2002-507738 A | 3/2002 |
| JP | 2002-181676 A | 6/2002 |
| JP | 2003-507715 A | 2/2003 |
| JP | 2003-83992 A | 3/2003 |
| JP | 2003-88367 A | 3/2003 |
| JP | 2003-536058 A | 12/2003 |
| JP | 2004-522979 A | 7/2004 |
| WO | 99/49295 A1 | 9/1999 |
| WO | 01/04634 | 1/2001 |
| WO | 01/13128 A1 | 2/2001 |
| WO | 01/40760 | 6/2001 |
| WO | 01/51909 | 7/2001 |
| WO | 01/94635 A2 | 12/2001 |
| WO | 03/012454 A1 | 2/2003 |

OTHER PUBLICATIONS

International Search Report for PCT/AU2004/000407, dated Jul. 9, 2004.

Supplementary European Search Report for EP03729710; dated Feb. 1, 2010.

English translation of Japanese Office Action for Japanese Application. No. 2009012244 dated Aug. 31, 2010.

Japanese Office Action dated Aug. 6, 2013 in Japanese Patent Application No. 2011-048799.

European Search Report dated Mar. 14, 2013 in corresponding European Application No. EP 12 17 1307.

\* cited by examiner

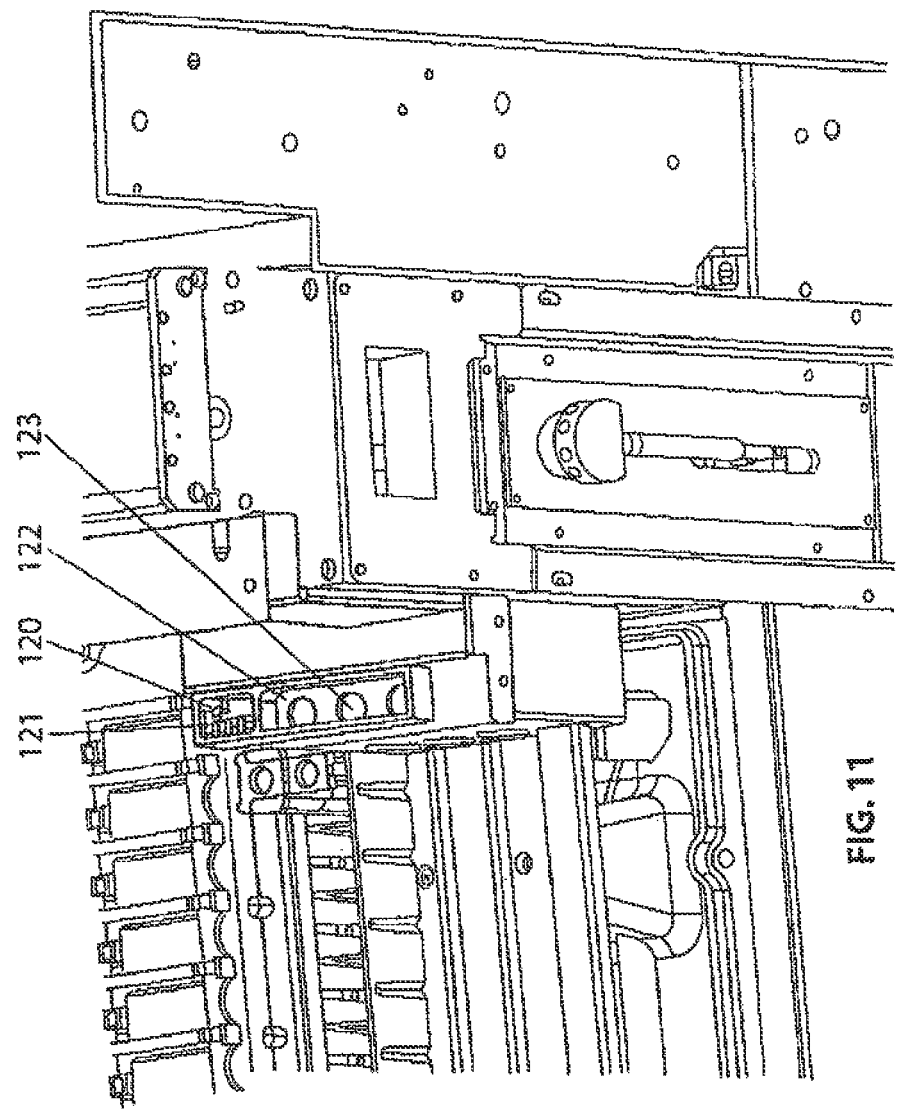

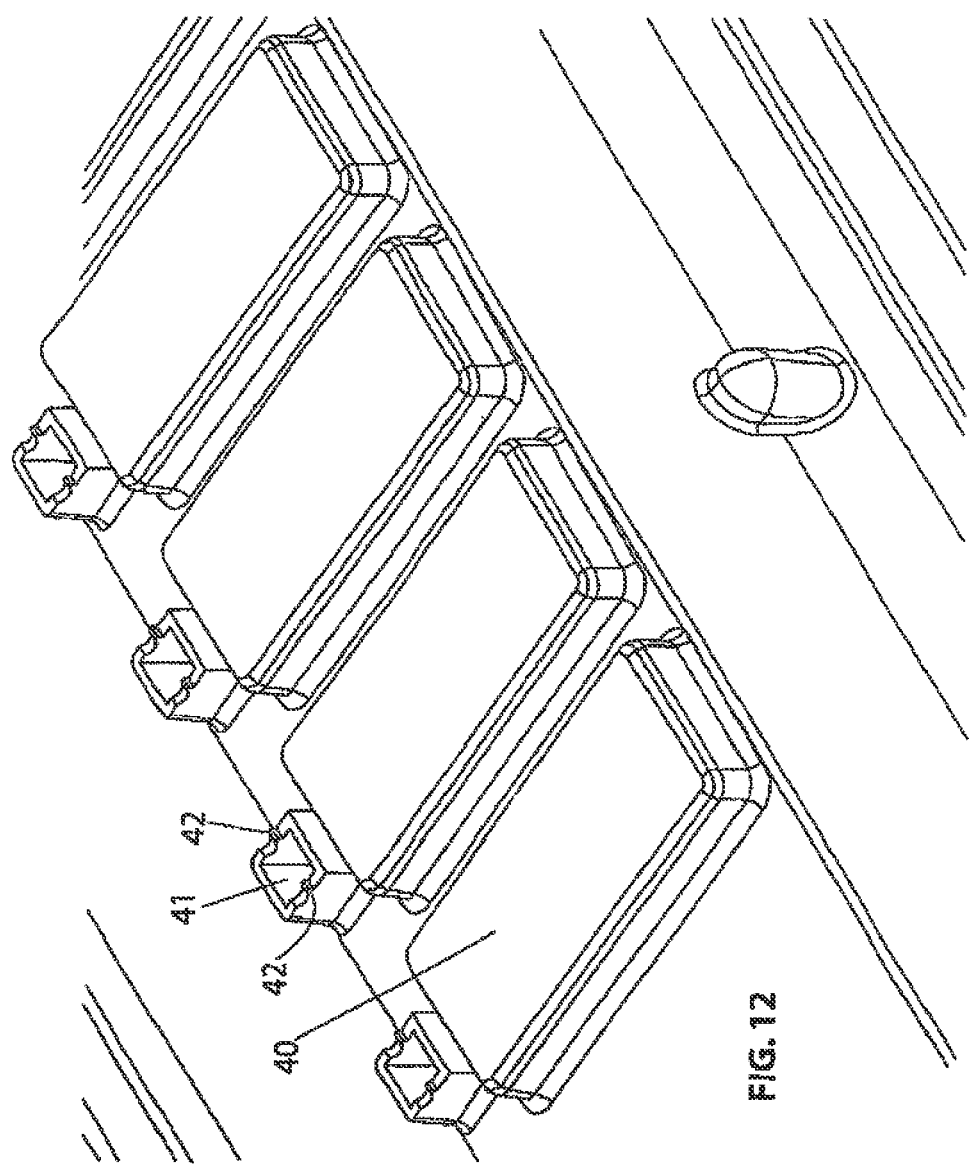

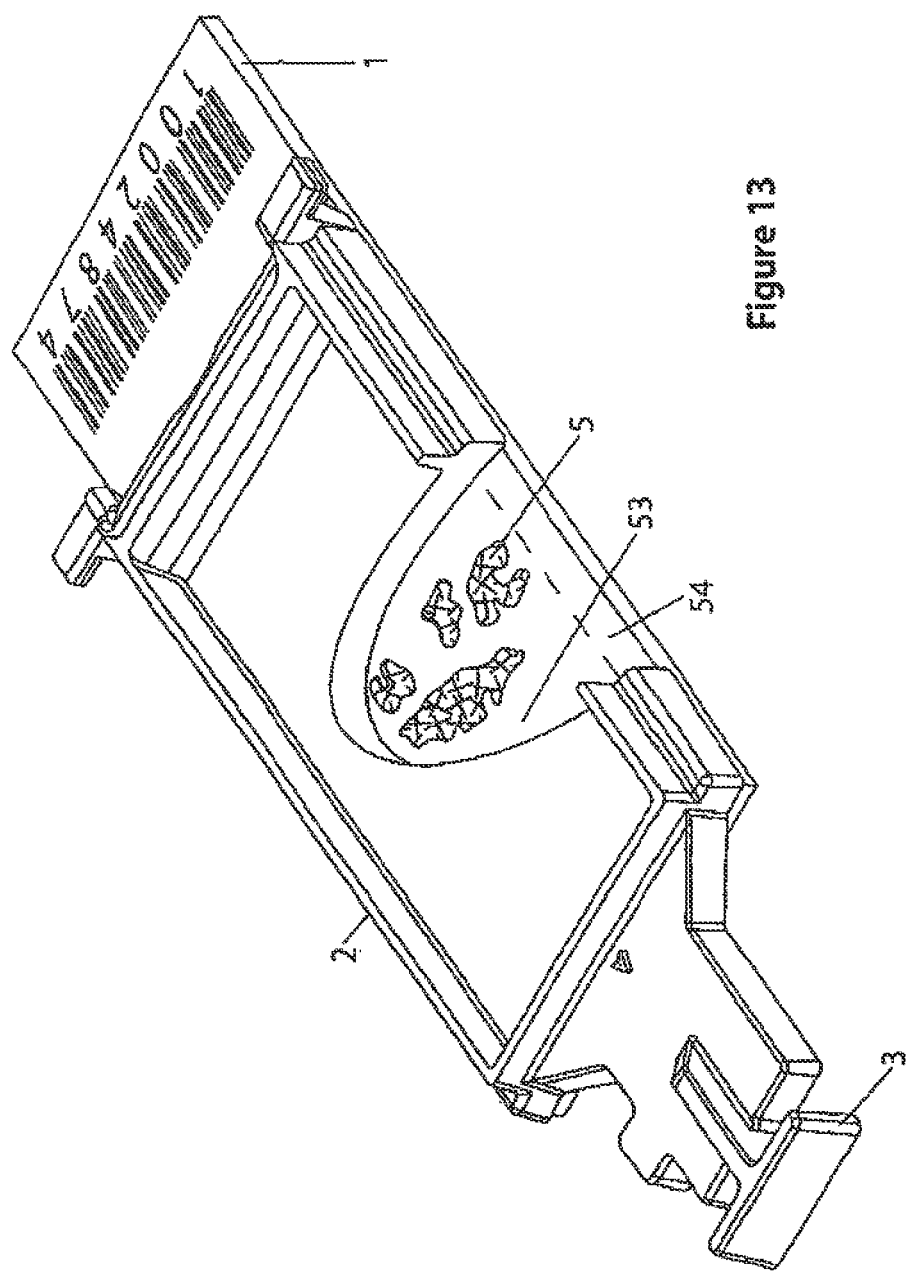

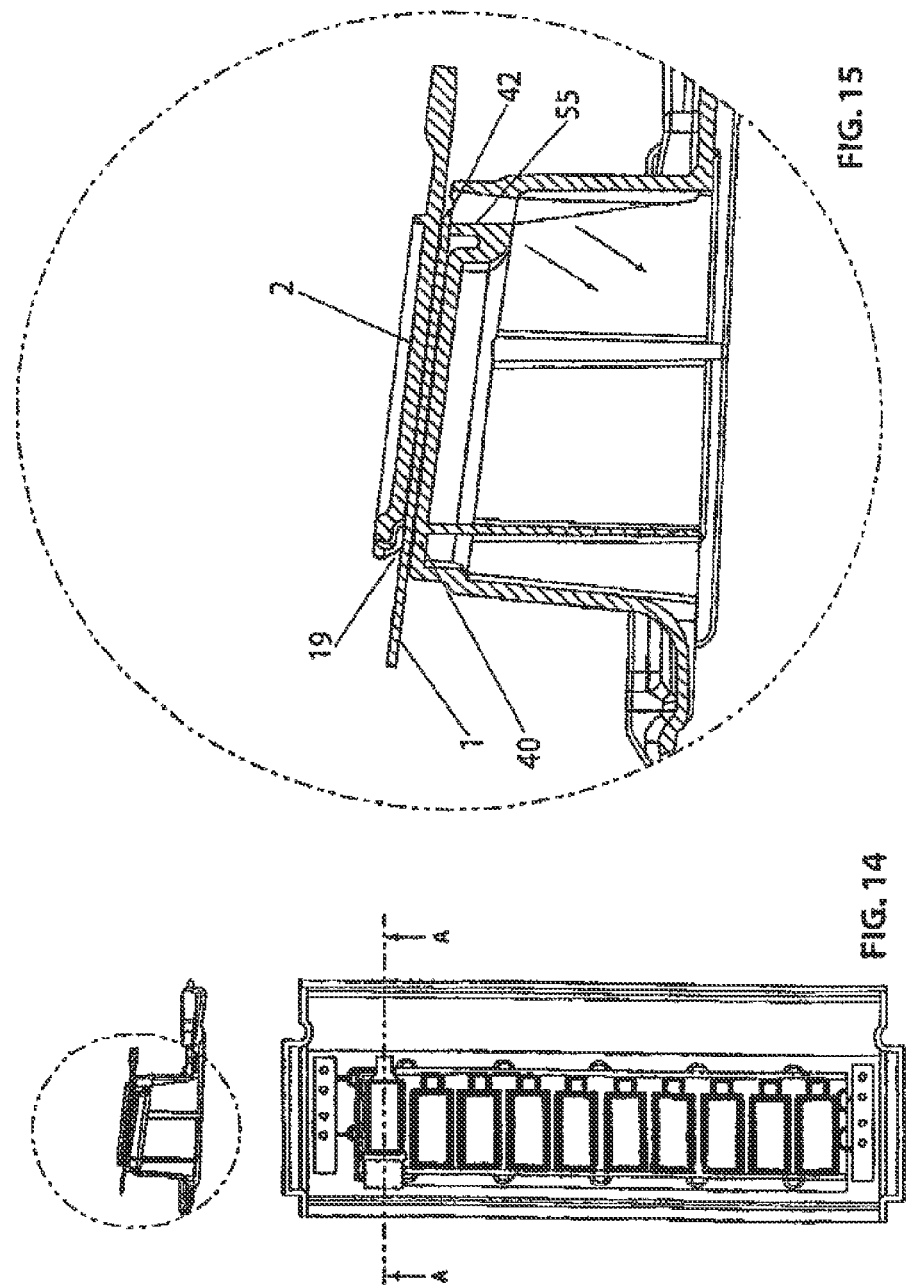

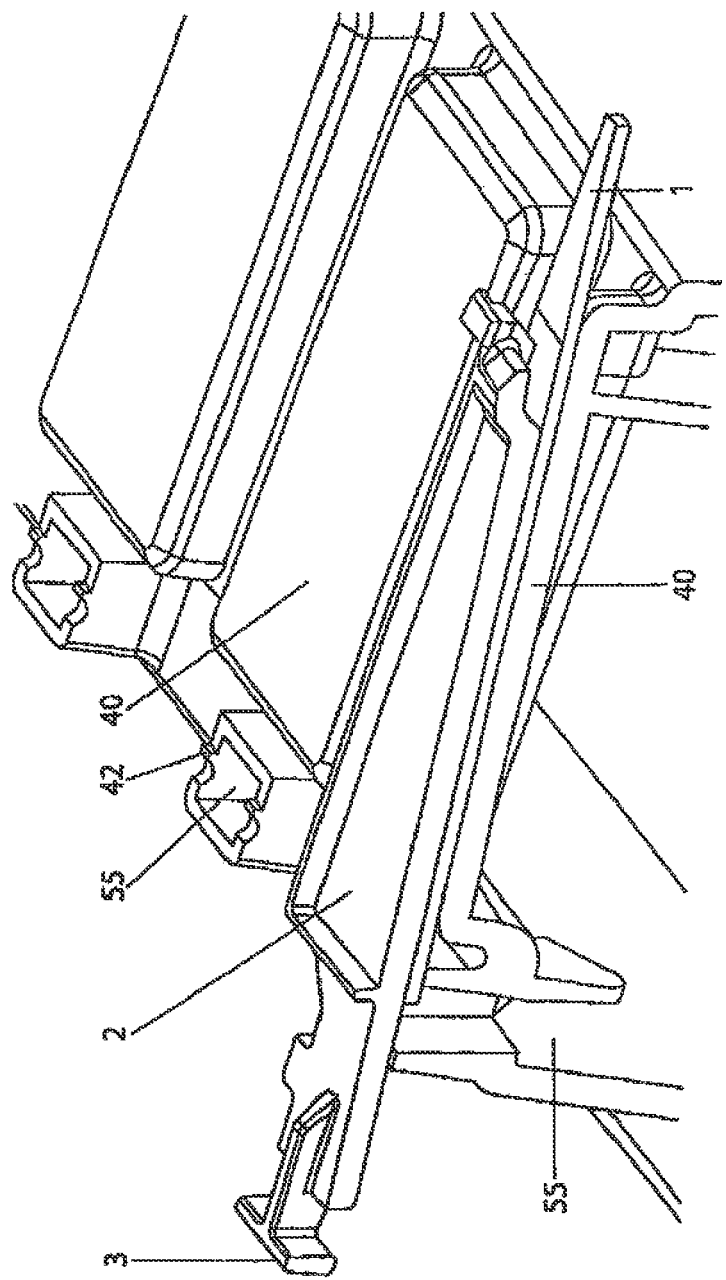

BIOLOGICAL REACTION APPARATUS WITH DRAINING MECHANISM

CROSS-REFERENCE OF RELATED APPLICATIONS

This is a continuation of U.S. application Ser. No. 12/697,684 filed Feb. 1, 2010, which is a divisional of U.S. application Ser. No. 12/560,850 filed Sep. 16, 2009, which is a continuation of U.S. application Ser. No. 10/518,626 filed Nov. 8, 2005, which is a national stage entry of PCT/AU2003/000779 filed Jun. 20, 2003, which claims priority from Australian patent Application No. PS3114/02 filed Jun. 20, 2002 and Australian patent Application No. 2003901871 filed Mar. 31, 2003. The entire disclosures of each of the above-noted prior applications are considered part of the disclosure of the accompanying continuation application and are hereby incorporated by reference in their entirety.

FIELD OF THE INVENTION

The present invention relates to a method or apparatus for providing a reaction chamber for chemical reactions. The present invention also relates to a method of filling a reaction chamber and a fluid used for this purpose.

BACKGROUND OF THE INVENTION

There are many applications where it is desirable to initiate a chemical reaction on a sample. Commonly the samples are located on a microscope slide. Typical reactions include immuno-histochemical reactions of cellular material, or in situ-hybridisation of DNA or RNA. In other forms, microarrays of thousands of small samples of material, including DNA, RNA proteins or small chemical compounds are attached to a microscope slide, where it is desirable to promote a chemical reaction between the material on the slide and other chemicals or fluids. These reactions require controlled conditions, including controlled reaction time, temperature and concentration of chemicals. It is important that the reaction across the slide is uniform, and also that reactions from slide to slide are consistent.

It is also important to minimise evaporation and overall fluid quantity used.

In the past, chemical reactions taking place on slides have been controlled by skilled persons adding and mixing the reagents. This allowed the time and quantity of the reagents to be controlled for each slide. However, this procedure is time consuming, required highly skilled operators, and can produce inconsistent results from slide to slide.

SUMMARY OF THE INVENTION

In one form, the present invention is a biological reaction apparatus for receiving at least one substrate having a sample located in a sample region, and a separate cover, such that a reaction chamber is formed between the cover and substrate over the sample region, wherein the apparatus includes
  a locating means to locate the substrate;
  a cover locating means for locating and moving the cover with respect to the substrate;
  a fluid dispensing means for dispensing fluid into the reaction chamber; and
  a draining mechanism;
wherein the draining mechanism includes wicking means.

Preferably the wicking means include points of contact on the substrate to provide a fluid path to drain fluid from the substrate.

Preferably the substrates are supported in the apparatus from underneath. Supporting substrates from underneath removes wicking paths from around the periphery of the substrate, which reduces fluid usage and loss.

In another form, the present invention provides a fill fluid for performing a filling of a reaction chamber, where the fill fluid has a viscosity higher than an antecedent fluid on a substrate.

Preferably the fill fluid is miscible with water

Preferably the fill fluid has a higher boiling point than water.

Preferably the fill fluid leaves no residue on the substrate or sample.

Preferably the fill fluid is inert to biological reagents and samples.

Preferably the fill fluid is a solution comprising glycerol.

In one form the fill fluid contains glycerol, water, and buffer. The buffer may be tris buffered saline.

Preferably the fill fluid contains between 2% to 80% glycerol by volume.

More preferably still the fill fluid contains between 10%-60% glycerol per volume.

More preferably the fill fluid contains between 20% to 30% glycerol.

In one form the fill fluid includes a surfactant to aid in the disbursement of any bubbles formed within the reaction chamber during a fill cycle.

More preferably the surfactant is Tween.

In another form the present invention relates to a receptacle for substrates having receiving means adapted to locate a substrate and a cover.

Preferably the receiving means includes stations to locate and support the substrate, and the cover is supported on the substrate.

Preferably the receiving stations support the substrate around part of a periphery of the substrate.

Preferably the receiving means are defined by a respective aperture having peripheral ledges for supporting the substrates.

Preferably the apertures are adapted to receive support platforms from a reaction apparatus, such that when loaded in a reaction apparatus, the platforms support the substrates.

Preferably the receiving means have a lifting means for lifting the covers from the substrate.

More preferably the lifting means are ramps adapted to engage with projections on the cover.

Preferably the receiving means have guides allowing the cover to be moved with respect to the receptacle and slide.

In another form the present invention relates to a dispenser for a reaction apparatus including a fluid conduit,
  a pump connected to the fluid conduit;
  a locating means for moving the fluid conduit from a fluid source to a dispensing region.

Preferably the dispenser includes a bar code sensor to detect the type of fluid source and substrate;

Preferably the dispenser includes a means for determining the volume of fluid remaining in a fluid source.

More preferably the means for determining the volume of fluid in a fluid source includes a sensor adapted to measure the level of fluid in a fluid container.

More preferably the sensor measures a change of capacitance of the fluid conduit to detect insertion into a fluid in the fluid container.

In another form the present invention relates to a method of dispensing fluid to a substrate including the steps of:
loading a reagent receptacle with at least one fluid container;
mounting the reagent receptacle to a reaction apparatus
detecting the reagent receptacle
once the reagent receptacle is detected, initiating a sensor to detect the type of fluid within the at least one fluid container
storing the information on fluid type to allow the fluid to be dispensed onto a substrate when required.

Preferably the sensor detects bar codes.

In another form the present invention relates to a reaction apparatus having a support projection for a slide, a dispensing means and a fluid removal means, where the support projection is adapted to support a slide from underneath, and a wicking means contacting the periphery of the slide, such that the wicking means provides a wicking path to remove fluid from the upper surface of the slide.

Preferably the support projection is angled between 0 and 10 degrees to the horizontal providing the apparatus with a fluid removal region. This provides a gradient to promote fluid flow.

Preferably the wicking means is wicking posts.

Preferably the wicking posts are located at the fluid removal region.

In one form the wicking means is adapted to extend across a significant proportion of the width of the substrate.

In another form the present invention relates to a reaction apparatus adapted to locate a substrate having a surface containing a sample and cover having a surface forming a reaction chamber with the sample containing surface, including a cover engaging means adapted to change the volume of the reaction chamber.

This promotes mixing of fluid within the reaction chamber.

In one form the cover engaging means is a clamping mechanism adapted to clamp the cover to the substrate.

In another form the present invention relates to a reaction apparatus having a separate substrate tray:
the substrate tray adapted to hold a number of substrates and covers;
at least one receiving station for receiving said substrate tray;
a dispensing means for dispensing fluid onto substrates in the substrate tray
wherein a reaction chamber is formed between the substrate and cover, such that fluid dispensed onto the substrates enters the reaction chamber.

Preferably the reaction apparatus has a number of receiving stations, each station adapted to receive a substrate tray.

Preferably the reaction apparatus has a controller which allows the fluid to be dispensed onto a substrate on one substrate tray independently of any other substrate tray.

In another aspect, there is provided reaction apparatus for receiving a substrate having a sample located in a sample region and a draining mechanism including wicking means for draining fluid from the substrate.

In another aspect, there is provided a method of forming a reaction chamber on a slide in a reaction apparatus including:
placing a cover having a cavity on a slide, forming a reaction chamber;
locating the cover and slide in a receptacle of a tray;
providing a receiving portion in the reaction apparatus having a mount for each receptacle in the tray;
loading the tray into a receiving portion of the reaction apparatus, where the receiving portion of the reaction apparatus locates the tray;
releasably holding the cover to the slide; and
releasing the tray from the slide and cover.

In another aspect, there is provided an apparatus for loading multiple slides and covers including:
a tray having a number of receptacles for slides and covers;
a receiving portion for receiving trays;
mounts for each receptacle located in the receiving portions;
a clamp for each mount;
wherein when a tray having slides and covers is loaded into the receiving portion, each clamp holds the cover on the slide to locate the slide, and the tray drops from the slides so each slide is supported by the mount.

In another aspect, there is provided a method of undertaking reactions on samples on slides involving multiple steps including:
loading a first holder having at least one slide into a reaction apparatus;
scanning the slide to determine the multiple steps in the reaction to take place on the slide;
determining whether other holders have been loaded into the reaction apparatus;
undertaking the multiple steps required on the at least one slide associated with the first holder;
when a second holder is detected, continue the steps in the reaction associated with the at least one slides in the first holder and then undertaking the at least one steps associated with the slides associated with the second holder.

In another aspect, there is provided an apparatus for performing reactions on slides including:
a tray having a plurality of receptacles adapted to support and locate slides and associated covers;
receiving ports for the trays, the receiving ports having mounts associated with each receptacle of the tray;
a clamping mechanism for clamping the cover and slide in place;
a fluid draining means for draining fluid from the reaction chamber formed between the cover and slide;
fluid receptacles to allow at least one fluid to be placed on the apparatus;
fluid dispensing means to dispense fluid onto the slides;
wherein once the tray is loaded, the slides and cover are clamped and the tray is moved so that the slides and covers are supported on the mounts, fluid may be dispensed onto the slides by the dispensing means, and drained by the draining means.

In another aspect, there is provided an apparatus for applying reagents to sample slides, including:
a plurality of ports for receiving the slides;
a reader for reading identification information on each of the slides; and
a reagent rack for receiving reagent containers which carry reagent to be deposited on the slides; wherein
the slides are provided on trays, which are received in the associated ports such that each tray represents a separate batch of slides, to allow for addition and removal of separate trays, for batch processing during operation of the apparatus.

BRIEF DESCRIPTION OF THE DRAWINGS

The invention is described, by way of non-limiting example only, with reference to the accompanying drawings, in which:

FIG. 11 shows a washing station for the reaction apparatus;

FIG. 12 shows a station of a tray receiving port and wicking means.

FIG. 13 shows a cut away section of a cover mounted upon a slide;

FIG. 14 shows a top view of a tray receiving port of the reaction apparatus of FIG. 1;

FIG. 15 shows a cross section of a slide and cover on a mount of a station;

FIG. 16 shows a cutaway view of sections of the slide, cover, and mount of FIG. 15.

DETAILED DESCRIPTION

Figure 1:
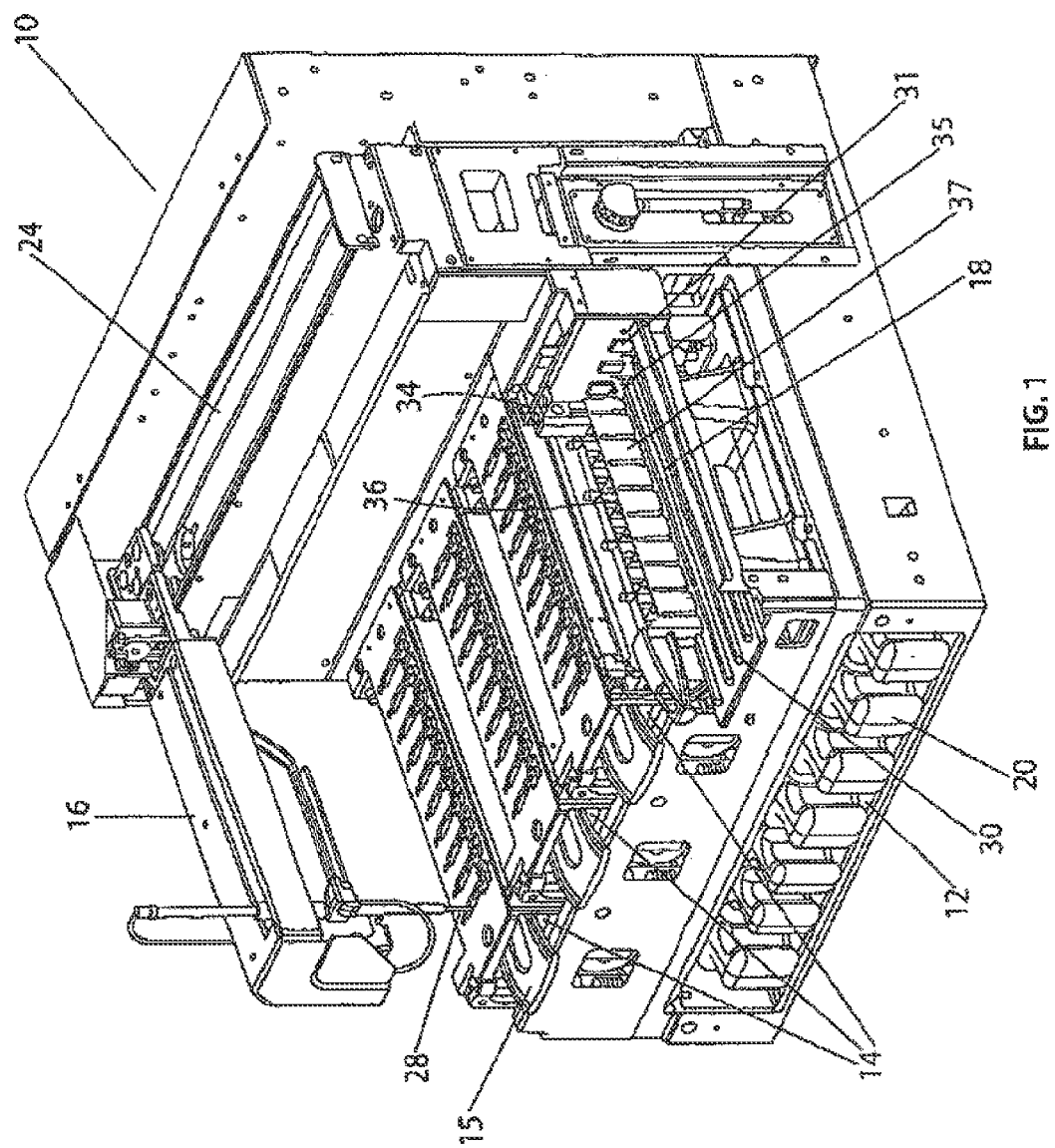
FIG. 1 shows an example of a reaction apparatus.

FIG. 1 shows an automated reaction apparatus 10 having bulk reagent container receiving zone 12, substrate tray receiving ports 14, a robotic arm 16 and a reagent rack receiving zone 18.

Bulk container receiving zone 12 is adapted to hold a number of bulk reagent containers 20. These containers 20 typically hold fluids such as tris buffered saline, PBS, Citrate, EDTA, organic solvents, waste reagents, deionised water, and dewaxing solutions. The bulk reagent containers of the apparatus 10 hold 1 to 4 liters of fluid.

Figure 5:
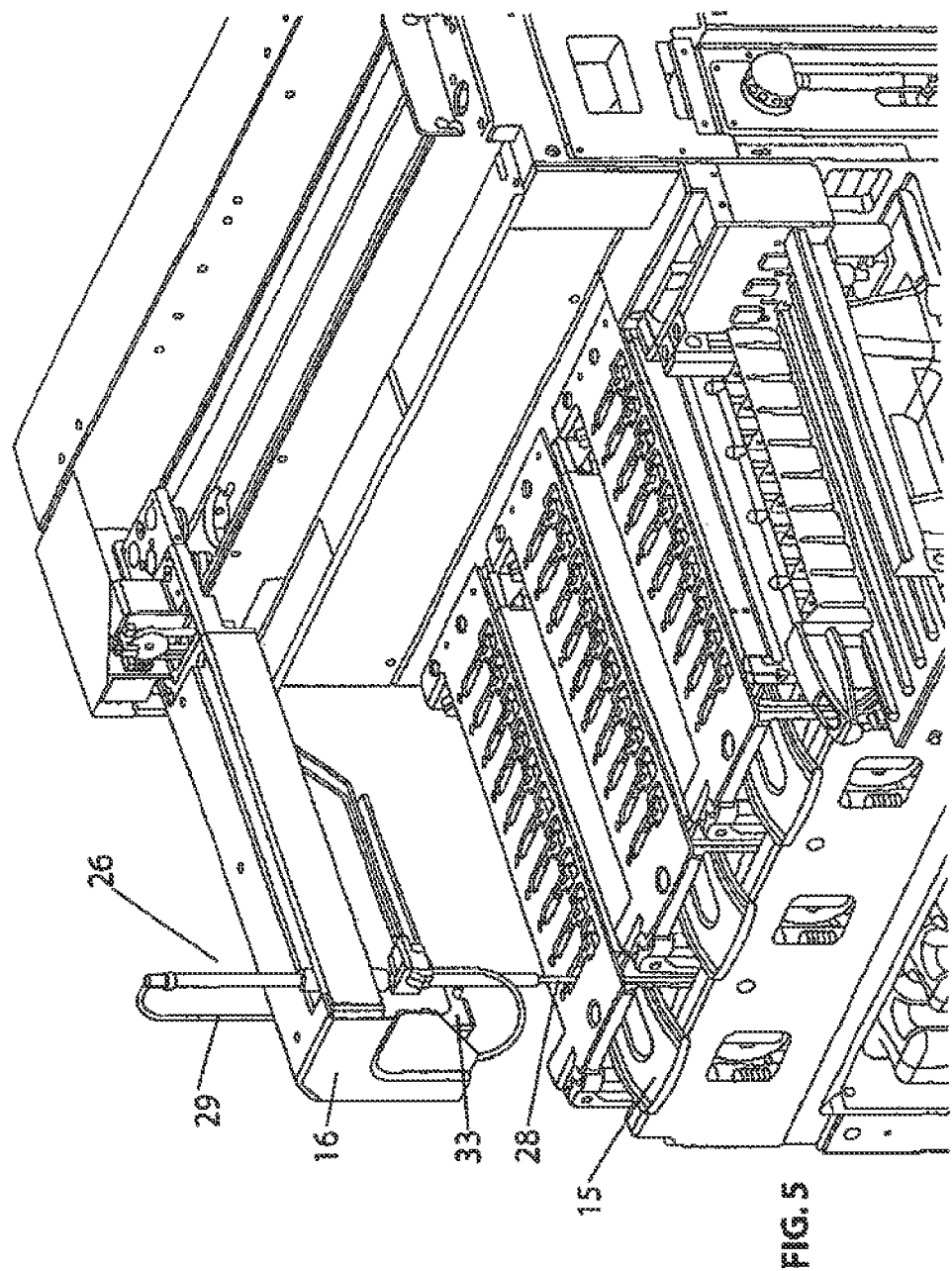
FIG. 5 shows a robotic arm and dispensing mechanism of the reaction apparatus of FIG. 1.

The robotic arm 16 is moveable along the guide 24, driven by motors (not shown) and controlled by a controller (not shown) such as a computer. As shown in FIG. 5 a dispensing means 26 is moveably mounted to arm 16, and includes a fluid conduit such as pipette 28, for dispensing fluids. The pipette 28 is attached by tubing 29 to a pump (not shown) which in this example is a motorised syringe pump capable of withdrawing, holding and delivering an accurate volume of fluid. The pipette 28 may be lowered when withdrawing or dispensing fluids, and raised when moving across the apparatus 10. A sensor 33 for reading bar codes is also included on the arm 16.

Figure 4:
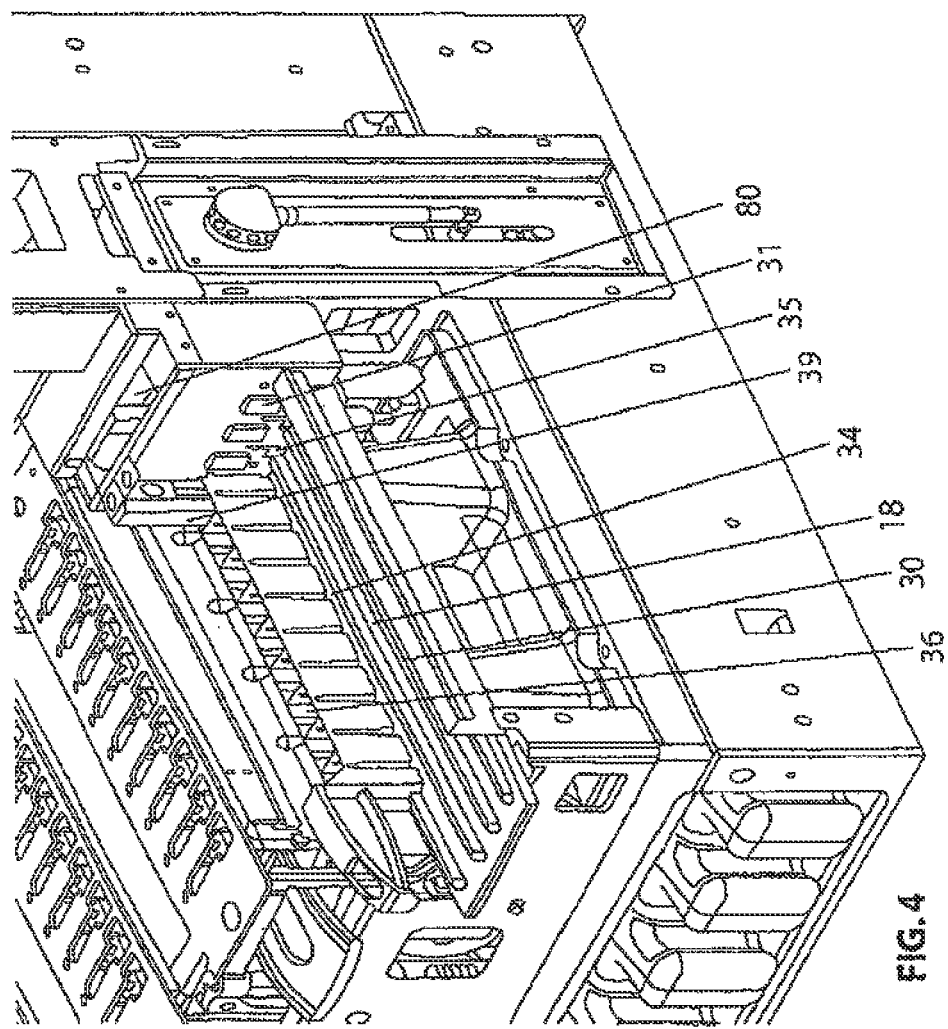
FIG. 4 shows an example of a reagent container rack and rack receiving zone of the reaction apparatus.

The reagent rack receiving zone 18 includes 4 rack mounts 30, rack locating clip 31 and a sensor 35 for detecting the mounting of each reagent rack 34, as best seen in FIG. 4. The reagent racks 34 each includes nine receptacles 36, each adapted to receive a reagent container 39. The reagent racks 34 may be removed from the rack receiving zone 18 when it is necessary to remove, refill or change a container 39.

Figure 3:
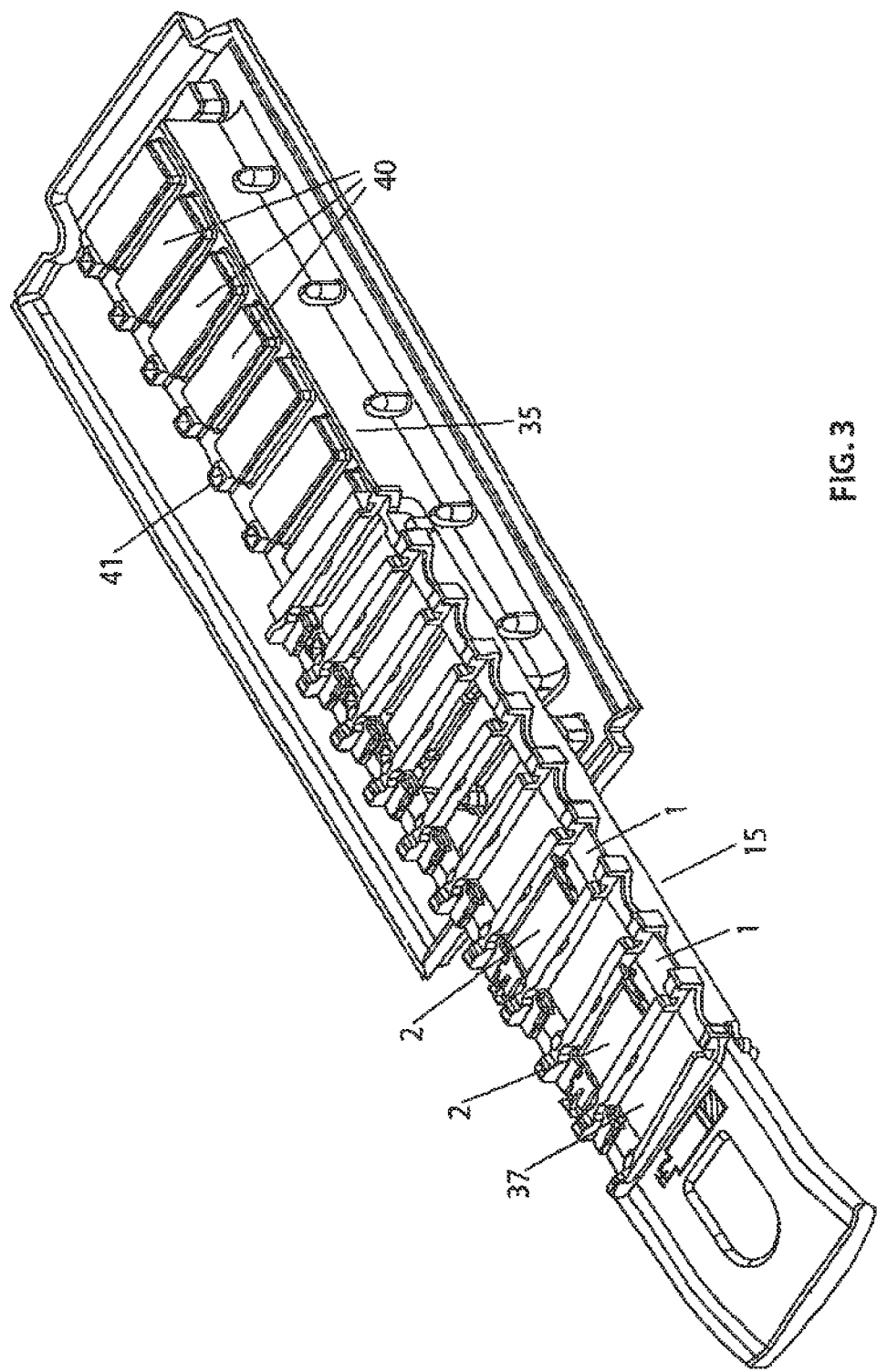
FIG. 3 shows the tray of FIG. 2 partially loaded into a receiving port of the reaction apparatus of FIG. 1.

In FIGS. 1 and 3 there are three slide tray receiving ports 14 and each is adapted to hold a single slide tray 15.

Figure 2:
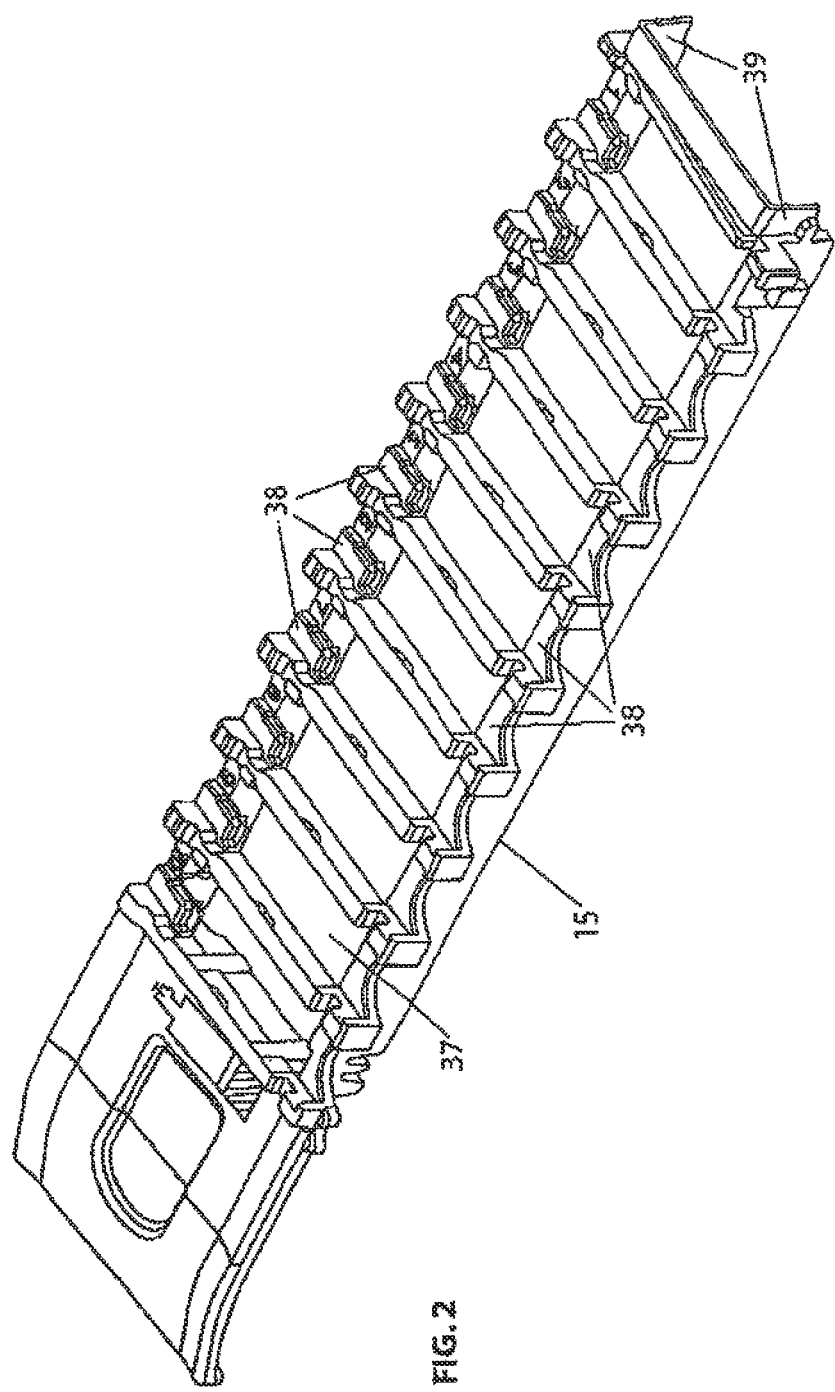
FIG. 2 shows an example of a tray used with the reaction apparatus of FIG. 1.
Figure 6:
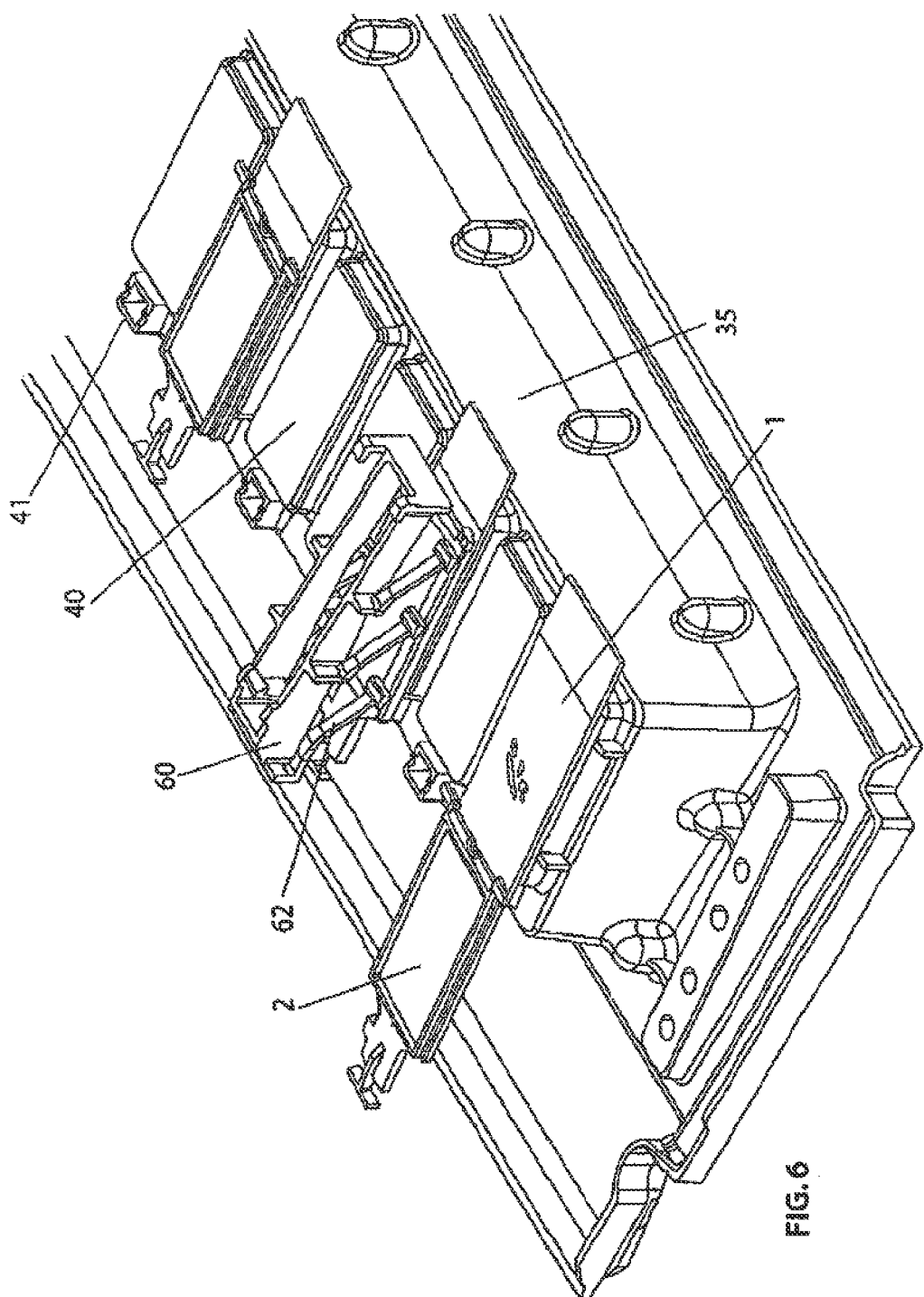
FIG. 6 shows slides and covers loaded onto stations of a reaction apparatus of FIG. 1.
Figure 7:
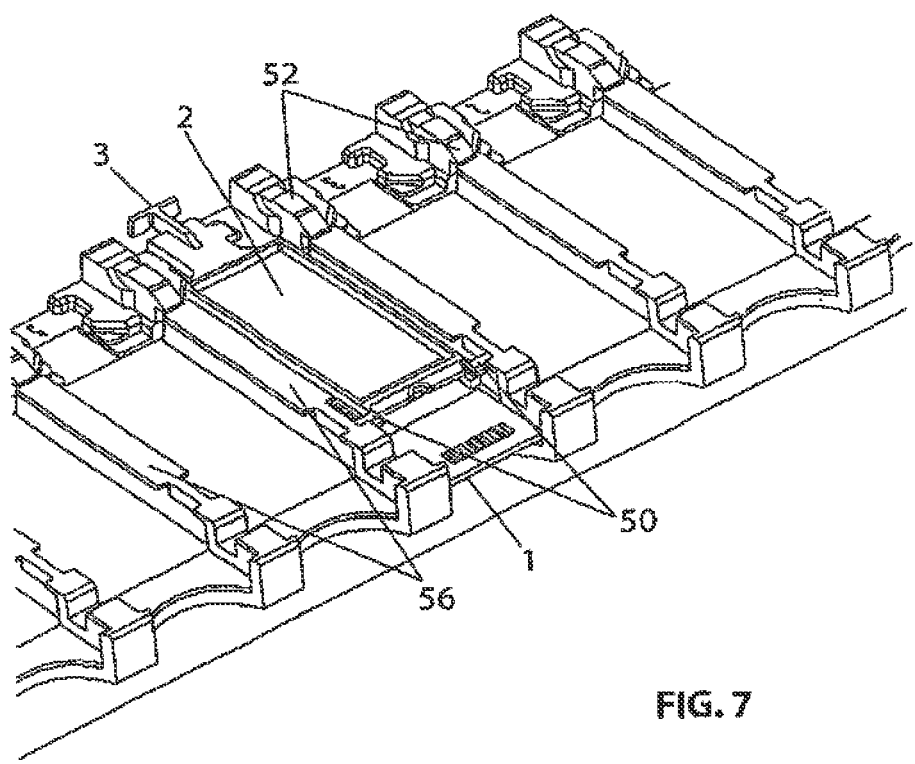
FIG. 7 shows a cover loaded into a tray shown in FIG. 2.

The slide tray 15 (shown in FIG. 2) includes ten slide receiving means 37, in the form of apertures which have support means 38. One or more substrates in the form of slides 1 may be placed into the slide tray 15, as shown in FIG. 3, such that the slides 1 are supported around the periphery but not in the middle. Covers 2 are placed onto the slides 1 as shown in FIG. 7. When the slide tray 15 is placed into the tray receiving port 14, each receiving means 37 corresponds to a slide station 35a in the apparatus 10 as shown in FIG. 6 and described in further detail below. A series of blocks 40 in the tray receiving ports 14 are adapted to support the slides 1 when the slide tray 15 is fully inserted into the apparatus 10 along rails 39a. When the slide tray 15 is inserted fully into the receiving port 14, it may be lowered such that the slides come into contact with and are supported by the blocks 40. The slide tray 15 is then not in contact with the slides, leaving the slides supported from underneath by the blocks 40. While only two slides 1 and covers 2 are shown loaded onto the tray 15 shown in FIG. 3, there may be any number of slides and covers, up to the number of receiving means 37 contained by slide tray 15.

The blocks 40, which are typically metal and may be controllably heated or cooled, support the slides 1 in conjunction with wicking means 41 in the form of wicking posts 42 as shown in FIG. 12. The upper surface of blocks 40 are inclined at a small angle to the horizontal (typically 5 degrees) to promote fluid flow along the slide during operation of the apparatus 10.

Figure 10:
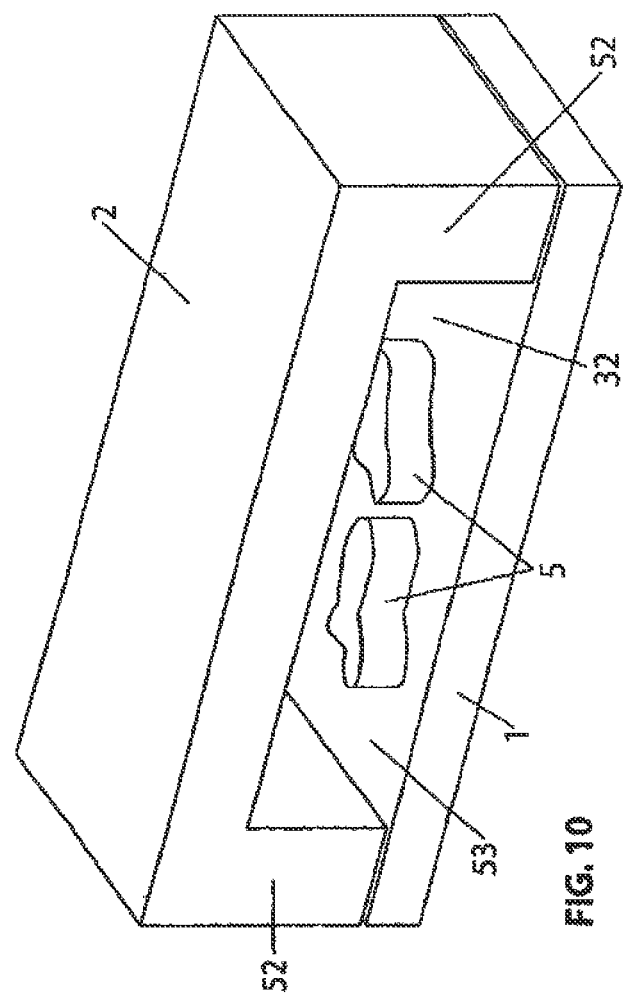
FIG. 10 shows a schematic section of a reaction chamber formed between a cover and a slide.

The cover 2 (best seen in FIGS. 8 and 13) is one of a number of variations possible, other variations being described in copending International patent application titled "A cover for a slide" by the same applicant and hereby incorporated by reference. The cover 2 is made from a clear plastic material, and is substantially the same width as the slide 1 to which it is to be mounted. A cavity 51 is located on side a of the cover 2 that faces the sample, and this cavity 51 in conjunction with lands 52 and sample holding surface 53 of the slide forms a reaction chamber 32 as shown in schematic FIG. 10, where the z axis has been exaggerated for clarity. FIG. 10 is a sectioned view of a cover over a slide 1 showing the reaction chamber 32, sample 5, lands 52 and slide surface 53. Typically the slide is 25 mm wide by 76 mm long, and the cavity is 100 micrometers high. The land 52 is in close proximity to or contacts slide surface 53 along contact surface 54 as shown in FIG. 13, and therefore restricts fluid leakage from the reaction chamber 32 outside the reaction chamber. Capillary forces assist in holding the fluid in the reaction chamber 32.

Figure 8:
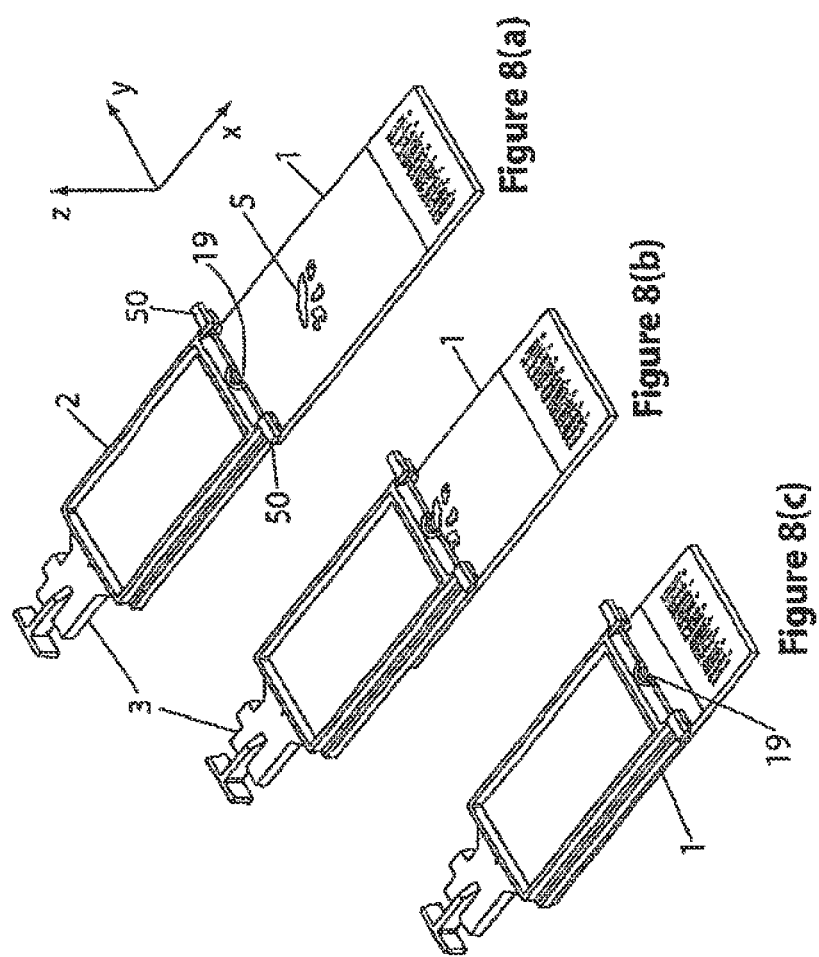
FIG. 8(a)-(c) shows a cover in three positions relative to a slide.
Figure 9:
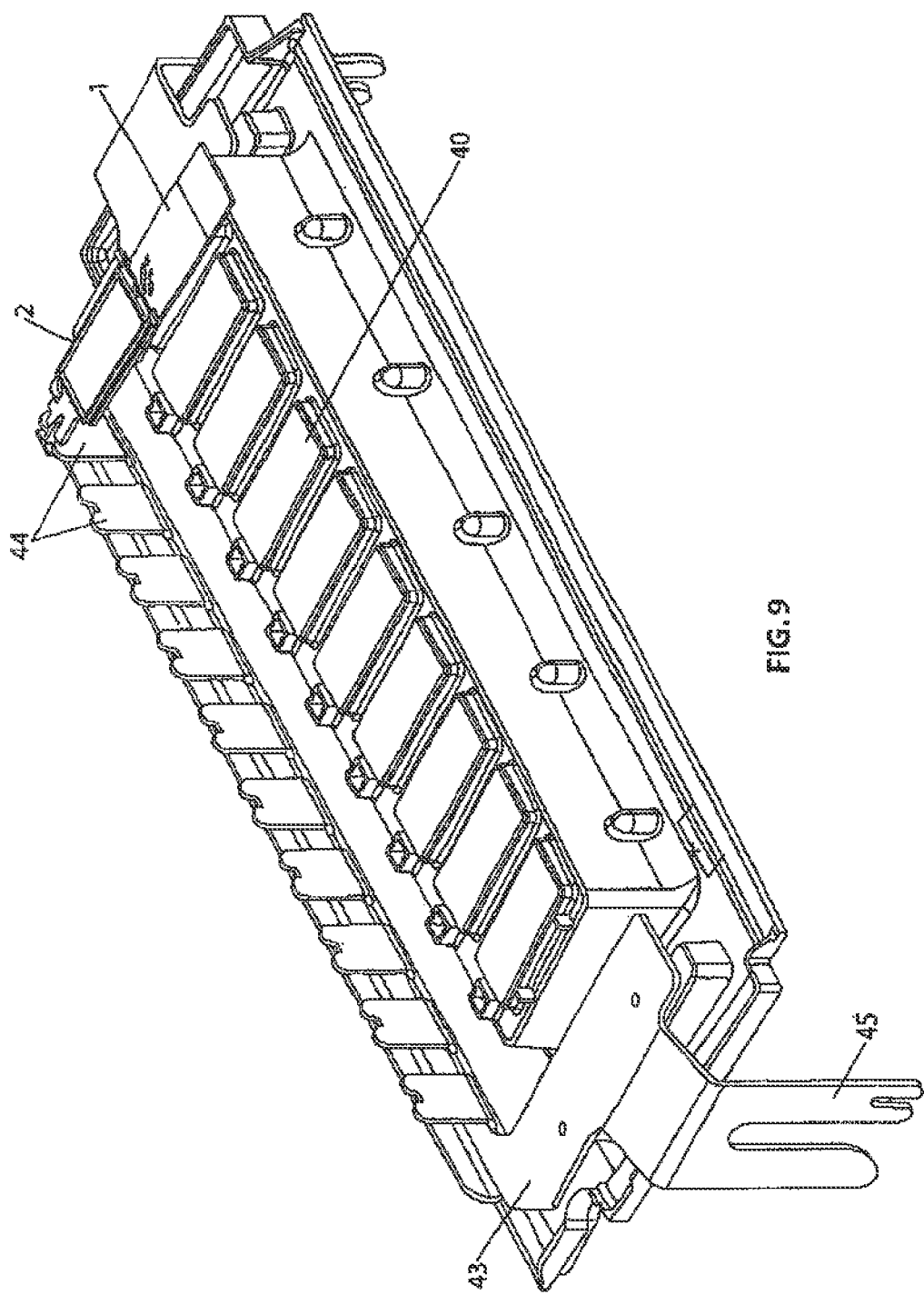
FIG. 9 shows a first view of an engaging means for a cover in a receiving port of the reaction apparatus of FIG. 1.

A locator arm 3 enables the cover 2 to be moved along the slide 1 by a locator engaging means 43 shown in FIG. 9. Each locator arm 3 is engaged by a bracket 44. A range of positions of the cover relative to the slides is shown in FIG. 8, where FIG. 8 (a) is fully open, FIG. 8(b) is partially open and FIG. 8(c) is fully closed. A reaction chamber 32 is formed between the cover 2 and slide 1 over a sample 5 on the slide 1 when the cover is in a closed or partially open position. The cover 2 includes a fluid reservoir 19 where fluid may be dispensed. There are several forms of fluid reservoir, as described in the abovementioned copending application. The cover and slide are capable of holding fluid in the reservoir 19. when the cover is in contact with the slide.

The fluid in the reservoir is drawn into the cavity 51 of the cover as the cover moves over the slide from an open position shown in FIG. 8(a) to a closed position shown in FIG. 8(c). The reservoir 19 may hold sufficient volume such that there is still fluid in the reservoir when the cover is in a closed position, and this provides a reservoir of fluid to reduce the need for fluid top ups during extended reaction times or sustained high temperatures. It is believed that the fluid is drawn into the cavity by a number of factors including capillary forces.

The covers 2 include wings 50 projecting from cover 2 adapted to engage ramps 52 on the slide tray 15, as shown in FIG. 7. The wings lift the cover 2 clear from the slide 1 when the wings 50 on the cover 2 engage lifting means in the form of ramps 52. It is possible to move the cover 2 to a position where the sample is uncovered but the cover remains in contact with the slide, along guides 56. Depending on the configuration of the ramps 52 and wings 50, it may not be necessary to completely open the chamber before the cover loses contact with the slide 1.

The arm 3 is moved by an actuator such as a cam arrangement (not shown) which engages positioning member 45 controllably so that the cover is able to be accurately positioned with respect to the slide along the x-axis shown in FIG. 8. While FIG. 9 shows that all covers are moved at once, in other examples of reaction apparatus it is possible to have individual control of the covers by moving arms individually.

In FIG. 6, slides 1 having bar codes 6 are shown on their respective blocks 40. For the purposes of this diagram the slide tray 15 and engaging means 43 have been omitted from view for clarity. A clamp 60 is used to hold a cover 2 securely in position on the slide 1 during a processing step. Clamp 60 includes a number of legs 62, which are situated around the periphery of the slide 1 and have spring like properties to provide an even force around the periphery of the cover. The clamp 60 may be made from a plastic material, and in another example (not shown) the legs may be made from metal, in the form of a spring (leaf or coil). Other forms of legs or clamp are possible such as compressible foam or pneumatic clamps.

The clamp 60 for each cover 2 may be raised when the cover 2 is to be moved, or lowered to engage the cover 2 during a fluid dispensing operation. In the present example, all clamps 60 and covers 2 in a particular receiving port 14 are moved together. Individual receiving ports 14 may operate independently of each other.

In use, bulk reagents in bulk reagent containers 20 are loaded into the apparatus 10. Reagent racks 34 having reagent containers 39 are loaded into the rack mounts 30. Sensors 35 detect their presence and the bar code sensor 33 reads the bar codes on each reagent container 39 to identify the contents of each reagent container 39 relative to its position in the reagent rack 34. Information relating bar codes 6 on slides 1 to samples on the slides 1 and bar codes 6 on reagent containers 39 relating to their respective contents, is input into the controller (not shown), which is typically a computer work station having an appropriate software interface and drivers. A slide tray 15 containing at least one slide 1, but up to ten slides, is placed into the receiving port 14, whereupon a sensor (not shown) detects the slide tray 15 and initiates a scan of the stations 35a. When scanning, the bar code sensor 33 on the robotic arm 16 moves to each station 35a and attempts to read a bar code 6. If a slide 1 with a bar code 6 is present, the controller compares the bar code 6 with a list of known slides and information input by the user to determine which protocol to apply to each individual slide 1. Alternatively, once the bar codes have been scanned, the user inputs information required for the apparatus to process the slide. Each slide may have a different protocol. The controller compares the reagents required to perform the reactions dictated by the protocols with the reagents located in the containers 39 in the reagent racks 34. Any discrepancy will cause an error message to be sent to the user. If a reagent container 39 is missing then the reagent rack 34 may be removed and the correct container 39 placed in the rack 34, whereupon the rack 34 is detected and another scan of reagent containers 39 is undertaken.

If no errors are present, the robotic arm 16 moves the pipette 28 of the dispensing means 26 to the appropriate reagent container 39 and withdraws the required amount of fluid. At this time the dispensing means 26 checks the capacitance of the pipette 28, which changes when the pipette comes into contact with the fluid surface of a reagent container 39. In this way the volume of fluid remaining in the reagent container 39 can be determined and the user can replace the container 39 as necessary. The robotic arm then moves the pipette 28 to a first slide 1 (determined by the controller) and dispenses the fluid onto the surface of the slide 1. There are several options in placement of the pipette 28 and cover 2 in relation to the sample 5 on the slide 1, and these will be discussed further below.

Once the dispensing operation for a first slide 1 has been undertaken, the process is repeated for further slides. It is not necessary for each slide 1 to be filled with the same fluid at each step, and the slides may be filled in any order that is appropriate. A washing station 120 shown in FIG. 11 is located near the reagent racks 34 and may be used to clean the pipette 28 prior to withdrawal of a different reagent. Washing station 120 includes a receptacle 121 for receiving the pipette 28, where cleaning fluid from one of the bulk reagent containers 20 is pumped onto the outside of the pipette 28 to remove traces of the previous fluid. Cleaning fluid may also be pumped from the bulk reagent container 20 via tubing to clean the inside surfaces of the pipette 28.

Reagents may be pumped from the bulk reagent containers 20 through piping and valves (not shown) into the pipette 28. Bulk reagent from the bulk reagent containers 20 may also by pumped to a wash station 120.

Other reagent containers such as the bulk reagent containers 20, included in the body 12 of the apparatus 10, can add to the type of reagents that may be dispensed onto the slide. Some bulk reagent containers 20 normally contain fluids required for washing and hydrating samples.

The reagent rack 34 may be used to contain a detection kit. A detection kit consists of a number of reagents in separate reagent containers 39 that are used to perform a particular test on one or more samples. Such a detection kit may include nine reagent containers 39 to perform a single test, and this reduces the number of reagent containers 39 available to other slides to twenty seven.

Typical reagents applied to samples on slides include primary antibodies, such as those sold by Novocastra Laboratories Ltd. These reagents are normally supplied in the reagent containers 39 in volumes typically between 7 ml and 30 ml. Other reagents and fluids, such as buffers and de-ionised water, may be kept in the bulk storage containers 20 which typically have volumes between 1-4 liters.

Some reagents, once prepared for application to a sample, have a relatively short shelf life. Therefore, either the reagent is supplied pre-mixed in a ready-to-use formulation, whereupon it must be used within a short period of time from ordering, or it may be prepared by laboratory staff prior to use, and placed into an appropriate reagent container. Some of the reagents, such as 3',3-diamino benzidene (DAB), when in a final form, begin to degrade soon after preparing and may not be useable more than 24 hours after initial preparation. This requires a new batch to be prepared every day, and ensuring that old batches are discarded after use. Further, enzymes such as protease may need to be applied in varying concentrations depending on factors such as tissue type, other reagents to be applied etc. This can result in numerous batches of reagents being required to be prepared before application to the samples, with the associated problems such as correct application, expiry date, correct mixing, tracking and traceability.

Concentrated primary antibodies may also require preparation before use, requiring dilution before application to a sample. Primary antibodies can be supplied either in a concentrated form or pre-diluted ready-to-use. However, it may be necessary to have several different working dilutions of the same antibody on a single apparatus 10, which would otherwise take up several locations in the reagent rack 34. It is therefore advantageous to have a single reagent container 39 of an antibody, where diluting of the antibody reagent may take place before the reagent is applied to the sample. The primary antibody may be diluted by a primary antibody diluent such as ABDIL 9352 sold by Vision BioSystems Ltd.

Figure 17:
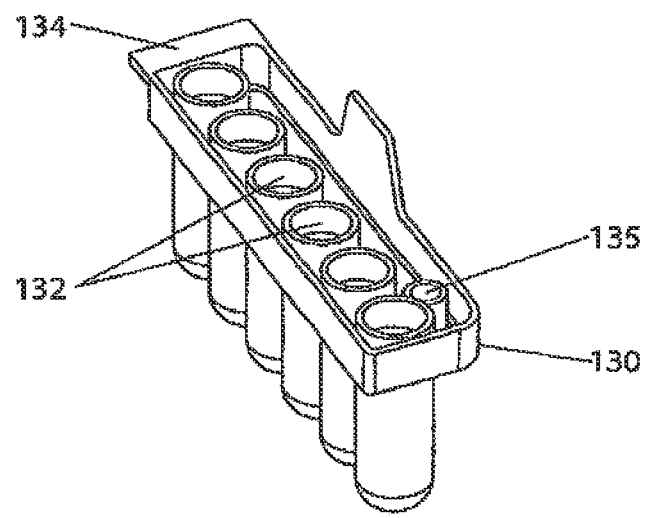
FIG. 17 is a perspective view of a mixing station.

In the present embodiment of the apparatus 10, a mixing station 122 is provided, as shown in FIG. 11. Mixing station 122 includes an insert 130, as shown in FIG. 17, having a number of mixing vials 132. The insert 130 has six vials, each vial able to hold a different reagent. The vials 132 are shown all the same volume, but may vary in volume according to requirements. Typical volumes may be 7 ml per vial.

Also mounted to the insert 130 is a tab 134. Tab 134 may be used to identify the insert 130 such as by way of a barcode. It is envisaged that as the insert 130 is disposable, but may contain a number of different reagents over the course of several runs of the apparatus 10.

The bar code on the insert 130 may be used to identify the insert 130 so that the controller knows when to discard the insert 130, and request that a new insert be loaded into the mixing station 122. This may be predetermined after a set period of time or uses.

Also shown on insert 130 is an overflow aperture 135, which is adapted to allow excess fluid to drain from the insert should any of the vials 132 overflow.

In use, information from the slide bar codes may be cross-checked with a database in the controller to establish which series of reagents is to be applied to each slide. The apparatus 10 then compares the reagents required, to the reagents currently loaded. If a reagent is identified that is not in final form for application to a sample, then a preparing step is scheduled into the order of tasks to be undertaken on the apparatus 10.

In one example, three reagent containers (identical to reagent container 39 located in the reagent rack 34) each have a component part A, B, and C of DAB may be located on the apparatus 10. In the present example DAB will be mixed in a ratio of 1 part A to 25 part B to 1 part C. To mix a batch of DAB ready for use, the robotic arm 16 first moves to the reagent container containing part A, and withdraws a set volume of part A of the reagent. The robotic arm 16 then moves to one of the vials 132 at the mixing station 122 and deposits the volume into one of the vials 132. The pipette 28 then moves to a washing station 120 located next to the mixing station 122, where the outside and inside of the pipette 28 are rinsed. Once cleaned, the robotic arm 16 moves the pipette 28 to the reagent container containing part B of the reagent. The pipette 28 withdraws the reagent (25 times the volume of part A) and moves to the vial containing part A. Once deposited in the vial, the pipette 28 moves to the washing station and is again washed, before moving to the reagent container holding part C of the reagent. The same volume as removed from the container holding part A is removed, and the pipette 28 moves to the original vial and deposits the reagent with the other reagents. Initially depositing the reagents into the mixing vials causes some mixing, however additional mixing can be accomplished by withdrawing some or all of the reagent from the vial 132 into the pipette 28, then re-depositing the reagent into the vial 132. The pipette 28 may move vertically to ensure that the tip is above the fluid level when depositing to aid the mixing process. The energy of re-deposition causes the reagents to mix more readily. This mixing process can be undertaken a number of times as desired. After the reagent has been mixed sufficiently, the pipette 28 may proceed to the wash station 120 if the next reagent to be applied to a sample is not DAB. This volume of the vials and the amount withdrawn by the pipette 28 provide a sufficient volume of DAB for many applications to samples. Whenever DAB is required, the robotic arm 16 moves the pipette 28 to the vial where the DAB was mixed, as the vial in which mixing of particular reagents is recorded by the controller. The time of the preparation is also recorded, so that after a predetermined period of time the mixed reagent can be discarded. This prevents the prepared reagent from being used after expiring.

After completion of testing for the day, or at the expiry of the DAB, the vial 132 containing the DAB (or any other reagent that has expired) can be cleaned as discussed below.

In relation to scheduling of mixing within a batch, specific details of scheduling are disclosed in Australian Provisional patent application titled "Method of Scheduling" filed 24 Feb. 2003 by same applicant, the contents of which are hereby incorporated by reference.

While the above process is automated, the resources employed (robotic arm 16 and pipette 28) may be utilised for significant periods of time in general reagent application to samples, and therefore it may be desirable to reduce the necessity to prepare several batches of reagent during a day. For this reason the apparatus 10 can be programmed to prepare reagents in the absence of any samples loaded into the apparatus 10 or during normal processing, and the volume and concentrations are user determinable through a user interface (not shown).

In the above example the concentration and time of preparation of each reagent in each vial 132 are stored in the memory of the controller of the apparatus 10, so there is no chance of old or incorrect mixed reagent being applied to a sample, reducing operator error.

The mixing by the pipette 28 ensures that the prepared reagent is fully mixed before application to a sample, and provides a better uniformity of mixing than, for example, applying components of the reagent directly to the sample and mixing on the sample.

Other examples of reagents that benefit from mixing on the apparatus 10 include protease, which may be required to be applied in a number of concentrations. In the above example, only one reagent container of protease would be required, and several concentrations of protease may be prepared by the apparatus 10 using diluent stored on board either in a reagent container 39 or bulk reagent container 20. These different concentrations may be placed in different vials 132 for later use.

In the above example, it is possible to have the mixing tasks scheduled into the steps of applying reagent to the samples. For example, there are often periods of time during a testing of a slide where there are no tasks required of the robot arm. These times may be referred to as open times, which typically occur when the fluid applied to a slide requires time to react before the next step is undertaken. If an open time is of a sufficient length, it may be possible to schedule in a mixing step. This minimises the time required to complete the application of fluid to samples, while freeing the operator from preparing the reagents.

After reagent is prepared, and it is applied to samples, remaining or expired prepared reagent is siphoned to waste by the aspirator. The vials 132 may then be cleaned. Cleaning is undertaken by draining any prepared reagent remaining after the required prepared reagent has been dispensed. Draining is done with the pipette 28, the drained fluid being directed to an internally plumbed bulk waste container. Once substantially empty, a rinse cycle is undertaken. The rinse cycle may use a cleaning solution, which for example could contain an alcohol such as IMS dispensed into the vial 132. The cleaning solution is then drained via the pipette 28. More than one rinse cycle may be undertaken. After removing cleaning solution for the final rinse, any remaining cleaning solution is allowed to evaporate to completely empty the vial.

It is also possible to revisit the mixing vial after a predetermined time from initial preparation, to re-mix the reagent. This may be done by withdrawing some of the prepared reagent into the pipette 28, and redispensing into the same vial 132. This may be important where components of the prepared reagent settle after time or do not stay mixed after a period of time. As with initial mixing, the remixing step may be scheduled during a period of inactivity of the robot arm and an aspirator.

When a slide tray 15 is loaded into the apparatus, each brackett 44 is engaging the locator arm 3 of each cover 2 in the slide tray 15. If an open fill is required, ie where the cover 2 is substantially or fully withdrawn from the slide 1, the locator engaging means 43 moves all covers 2 on the slide tray 15 off the slides to a position such as that shown by cover 2 in FIG. 8(*a*). This open position of the cover 2 exposes the sample 5, whereupon the pipette 28 may be positioned in a variety of positions. The positions of the pipette 28 include either over the sample 5, to dispense fluid directly onto the pipette 28, or adjacent the front of the cover 2 into a fluid reservoir 19 shown in FIG. 8. The reasons for each position will be explained below.

In an open fill situation, once the fluid has been dispensed on all slides, the locator engaging means 43 moves to position the reaction chambers 32 over the samples on the slides. Capillary action and the movement of the cover 2 over the surface of the slide 1 causes dispensed fluid to flow into the region between the cover 2 and slide 1. The clamp 60 may be used to hold the cover 2 in place and prevent it from floating on the film of liquid between the cover 2 and slide 1.

When the slide 1 is on the block 40, it may be in contact with wicking posts 42, as shown in FIGS. 14 and 15. Movement of the slide 1 on the block 40 is possible as slide lengths vary, and movement of the cover 2 over the slide can move the slide 1. Normally this movement is only in the order of 1-2 mm. In another example (not shown) it is possible to use an actuator to move the slide away from the wicking posts to reduce wicking of fluid from the reaction chamber.

FIG. 15 shows the cover 2 on the slide 1, both located on block 40. The wicking posts 42 are in contact with the slide and therefore provide a wicking path for fluid. The reaction chamber is located between the slide and cover but as FIG. 15 is approximately to scale, it cannot be clearly seen in this view. Fluid entered in fluid reservoir 19 flows into the reaction chamber and may flow from the reaction chamber down drain 55 associated with the wicking posts 42. To assist in fluid clearance, the air pressure around the wicking posts may be lowered by withdrawing air from the drain 55 by a pump such as a fan (not shown). This will promote fluid flow through the reaction chamber and out the drain 55 if required. Withdrawing the cover from the slide will also promote fluid flow down the drain 55.

The wicking posts will wick fluid even if not touching the slide, as the meniscus of the fluid will extend out from the edge of the slide near the wicking posts if there is fluid pressure from the wicking posts, or if the air pressure in that region is reduced.

The wicking action may, however, be interrupted if required, such as during an incubation period, by manipulating the locator arm 3 so as to move the cover 2 away from the wicking posts 42 a distance sufficient to prevent any further drain of fluid from the reaction chamber.

When dispensed fluid fills the reaction chamber 32 there may be fluid contact between the fluid in the reaction chamber and the wicking posts 42. The upper surfaces of the blocks 40 are at angles approximately 5 degrees to the horizontal with the end of the slide adjacent the wicking posts lower than the bar code end of the slide. The angle promotes fluid flow towards the wicking posts 42, which provide the only contact with the slide 1 apart from the block 40. As the wicking posts 42 contact the slide 1 at or near the upper surface of the slide 1, at the lowest end of the slides upper surface, the fluid will tend to wick from the area in the reaction chamber on the slide adjacent the wicking posts 42 and not from other areas, as there are no other wicking points.

It is possible to control the dispenser 26 to dispense fluid onto the slide in various positions. The fluid may be dispensed towards the bard coded end of the slide, or towards the wicking post end of the slide if the cover is in an open position. It is also possible for the dispenser to dispense in a "staggered waterfall" arrangement where fluid is dispensed in a number of positions up the slide. The cover may close as the dispenser moves up the slide.

Fluid is dispensed onto the slide 1 in controlled volumes. It has been found that in the current arrangement, fluid does not wick from the reaction chamber 32 down the wicking posts 42 unless one of two conditions are met. Firstly, there needs to be fluid in the reservoir 19 to push fluid through the reaction chamber 32. The additional fluid displaces the antecedent fluid, which is removed from the reaction chamber. The antecedent fluid is removed from the reaction chamber via the wicking posts. Thus it is possible to replace a fluid in the reaction chamber by placing fluid in the fluid reservoir. Secondly, a pump can produce a reduced atmospheric pressure around the wicking posts to cause the pressure differential to draw fluid from the reaction chamber. The reaction chamber may also be drained by reducing air pressure around the wicking posts.

If no new fluid is to be added to the reaction chamber it is possible to drain the reaction chamber by opening the reaction chamber. This is accomplished by sliding the cover along the slide 1 until the sample is uncovered. The fluid in the reaction chamber will tend to follow the cover off the sample, draining the fluid via the wicking posts. Alternatively, it is possible to turn on the fan to draw fluid from the reaction chamber, where the cover can remain in a closed position. A combination of the above is possible.

In some cases, such as where the fluid being applied or in the reaction chamber is particularly viscous, it may be necessary to utilise the pump and apply fluid to the reservoir to cause fluid flow through the reaction chamber. In this way it is possible to change over fluid a controlled way.

The cover 2 and slide 1 are removed from the apparatus 10 when the reaction is complete and therefore the reaction chamber 32 is unique to each reaction. This eliminates the necessity to thoroughly clean a static reaction chamber as required in other apparatus. Further, the reaction chamber is substantially sealed to the environment reducing evaporation and the possibility of the sample drying out.

As the reaction chamber is formed from a slide and a replaceable cover, it is relatively inexpensive to form a reaction chamber, and a new, clean reaction chamber is formed for each reaction, reducing cleaning costs and time, as well as eliminating the possibility of cross contamination with previous reactions or cleaning fluids.

The initial fill with the cover withdrawn (open fill) provides a method of filling the reaction chamber while minimising the formation of voids or bubbles inside the chamber. Due to the reaction chamber having a depth of approximately 100 microns, once the cover is over the slide forming the reaction chamber, it is difficult to flush the chamber of bubbles or voids. Some of the fluids used in the reactions are extremely expensive and may be hazardous, and therefore it is desirable to keep their consumption to a minimum.

A suitable initial fill fluid has been found to be a mixture of water and 25 to 30% glycerol. Small amounts of glycerol do assist in reducing the incidence of bubble formation, as do larger amounts, however it has been found that in some circumstances 25% glycerol by volume works well. Additives such as detergents (Tween for example) may be included to reduce surface tension, which also have proved beneficial in removing voids in some circumstances.

The use of glycerol reduces the propensity of the fluid to wick from the surface of the slide via extraneous wicking paths. This reduces the number of large voids that form during an initial fill.

To assist in removing any voids that may reside in the reaction chamber after an initial fill, it has been found that a fluid having reduced surface tension and viscosity, but miscible with water, such as an alcohol like isopropanol, is useful as a flushing fluid.

Typically flushing occurs after a heating phase, as increasing the temperature in the reaction chamber can cause bubbles or voids to form. The use of a low viscosity fluid such as isopropanol can assist in moving the bubbles or voids.

Once the reaction chamber is filled with fluid, it is possible to add further fluid without entrapping additional air. Thus, it is possible to change fluids by merely topping up the fluid reservoir, and in some instances, reducing air pressure near the wicking posts. The reaction chamber thus formed exhibits some desirable flow characteristics, in that a new fluid will not tend to mix with the fluid it is replacing. The capillary nature of the reaction chamber does not allow significant turbulent mixing and therefore it is possible to accurately time the changing of fluids without requiring extensive flushing of the chamber or slide surfaces. This allows the start and finish of a reaction to be determined with sufficient accuracy across a range of reactions and fluids.

The speed of the cover movement and pressure reduction can effect the volume of residual fluids left behind.

In order to promote reactions in the reaction chamber on the sample, it is possible to move the cover vertically (in the z axis direction as shown in FIG. 8) on the slide by modulating the load on the clamp 60. The vertical movement assists in mixing the fluid in a vertical direction as well as a direction across the slide (y-axis direction), rather than along its length. Filling and draining the reaction chamber move fluid along the length of the slide (x-axis direction) and this may be assisted by moving the cover along the x-axis of the slide by moving the arm 44. The blocks 40 may be heated to promote the reaction.

It is desirable in many reactions, for example involving in-situ hybridisation, epitope retrieval, or dewaxing, to heat the fluid in the reaction chamber to a temperature approaching 100 degrees Celsius. In this situation, gas bubbles have been known to form, and the gas bubbles can be difficult to shift. If the bubbles occur on the sample they reduce the amount of fluid exposed to the sample, and can therefore effect the consistency of the result within a sample, as well as between samples on different slides. In such situations it has been found that using covers having one or more coatings can reduce the incidence of bubble formation.

Another feature of the reaction apparatus 10 is that the size of the reaction chamber may be varied. Typically the volume of the reaction chamber when the cover is completely over the slide, termed the closed position, is 150 microliters. However, if the cover is not completely closed then the reaction chamber formed between the cover and slide may be of reduced volume. In FIG. 8(b) a cover in a partially closed position is shown, wherein the volume of the reaction chamber would be significantly reduces, for example to 80 microliters. This example may be useful where samples are small, or placed towards an end of the slid that allows the cover to form a smaller reaction chamber while still covering the sample. Smaller reaction chambers require smaller volumes of fluids, which is advantageous if the fluids used are expensive or difficult to obtain. The examples of the reaction apparatus allow the position of the cover to be referenced when dispensing fluid onto the slide. Therefore, when the cover is in the open position, it is possible to dispense fluid either on top of the tissue sample, or between the tissue sample and the cover, so that movement of the cover to a closed position pushes fluid across the sample while filling the reaction chamber. It is also possible to dispense fluid at a number of positions along the slide, or to dispense fluid on or near the front edge of the cover.

The following is a description of set up and use of the above-described apparatus.

1. Slide Loading:

Paraffin-embedded tissue sections (sample 5) mounted onto glass slides are loaded into the slide tray 15 with covers 2 and inserted into the receiving zones 14 of the reaction apparatus 10. The user selects desired protocols, run type [ie 100 μL (economy—⅔ of slide) or 150 μL (standard-full slide)] and ensures that the reagents trays 34 containing the necessary reagent containers 39 are loaded into the apparatus 10.

2. Dewaxing:

Removal of wax from tissue sections following sectioning is required prior to performing staining procedures. For dewaxing on the instrument the cover remains in a closed position while dewaxing solution is dispensed by the dispensing means 26 onto the slides, which are pre-heated to 70° C. by mounting blocks 40. Slides are incubated for 4 min at 70° C. prior to removal of excess dewaxing solution by reduced air pressure around the wicking posts caused by a pump (not shown). Fresh dewaxing solution is dispensed onto the slides for incubation at 70° C. for a further 4 min. This process is typically repeated once more for all slides in a tray that require dewaxing. Slides are cooled to ambient temperature and covers opened and closed to remove excess dewaxing solution containing residual dissolved wax. All slides are washed with isopropanol applied by the dispensing means one slide at a time, to remove remaining dewaxing solution, and then all slides are rehydrated with distilled water dispensed by the dispensing means.

3. Epitope Retrieval:

Before IHC and ISH processing can take place, it is necessary to expose epitopes (proteins, DNA, RNA) within the tissue which may have become hidden during the fixation process. On the instrument two protocols may be present:

a. Heat-Induced Epitope Retrieval (HIER)

Following dewaxing, all slides receive an initial fill of retrieval buffer (initial fill fluid) (10 mM Sodium Citrate/ 30% Glycerol/0.05% Tween) with the cover in the open position to facilitate movement of solution down the slide and reduce bubble formation. Covers are closed and mounting blocks 40 heat the slides to 100° C. for the required retrieval time. After retrieval is finished, slides are cooled by individual flushing with retrieval buffer by the dispensing means.

b. Enzyme-Induced Epitope Retrieval (EIER)

Protease solution (ie proteinase K, pepsin, and trypsin) is dispensed onto each slide by the dispensing means and incubated for 10-30 minutes at the desired retrieval temperature (for example ambient-50° C. or room temperature). After retrieval is complete, each slide is washed with distilled water dispensed by the dispensing means.

4. Immunohisochemistry (IHC):

IHC is based on specific binding of antibodies (proteins) to antigens (proteins) in tissue biopsies and specimens. Following the epitope retrieval stage, each slide receives buffer containing Tween-20 from the dispensing means. Each slide may be treated with hydrogen peroxide for 8 min at ambient temperature to block endogenous peroxidase activity within the tissue sections and is washed with TWB buffer containing Tween-20, again dispensed by the dispensing means. A primary antibody directed against a specific target protein is applied by the dispensing means to the tissue sample and incubated for 15-60 min. This is followed by a secondary biotin-labelled antibody incubation. Bound antibody is detected by dispensing streptavidin- or alkaline phosphatase-conjugated peroxidase onto each slide, which is visualised by addition of a chromogen (ie DAB, BCIP/ NBT), all by dispensed by the dispensing means. Sections are counterstained with hematoxylin, also dispensed by the dispensing means.

5. In Situ Hybridisation (ISH):

ISH allows the detection of specific nucleic acid sequences within a cell. Following the EIER stage, tissue sections are dehydrated by dispensing isopropanol into the reaction chambers of each slide and the cover moved to the open position to dry the tissue. A fluorescein- or biotin-labelled nucleic acid probe is applied to the slide and the cover closed slowly to distribute the probe evenly across the tissue. The probe is allowed to hybridise to its complementary DNA/RNA target in a tissue section for 1.5-2 hours at 37-55° C. Where the target is DNA, the tissue section and probe are first denatured at high temperature (ie 95° C.) for 5-10 min prior to hybridisation. Slides are washed by dispensing TWB from the dispensing means using a staggered waterfall rinse to gently remove unbound probe. Following washing, the cover is moved to the closed position for the remainder of the procedure. Bound probe is detected by applying an anti-fluorescein or anti-biotin antibody conjugated to alkaline phosphatase, dispensed from the dispensing means, which is visualised by addition of an enzyme substrate (BCIP/NBT), also dispensed from the dispensing means.

6. Removal:

Once the protocol has been completed for a particular slide tray, the tray may be removed regardless of the status of the other slide trays. As the slide tray may contain slides each having different protocols applied, the tray must remain in the apparatus until all protocols for that particular tray have been completed. An indicator such as a light informs the user when all the protocols to be applied to the slides on the slide tray have been completed.

Once the reaction chamber has been filled it is possible to hold the sample in a buffer for an extended period of time. Fluid in the reaction chamber can be topped up if, for example, some slides reactions are completed but other slides on a slide tray require additional processing. Having three slide trays allows a certain amount of flexibility in that samples that require time intensive processing can be placed in one slide tray, while faster processing may be undertaken on a separate slide tray. An additional slide tray may be entered while one or more slide trays have begun processing, and it is possible to remove a finished slide tray while another slide tray is being processed. The reagent racks 34 may be removed during a process run, if for example, a container empties. Once the reagent rack 34 is replaced, the bar code sensor 33 scans the bar codes on the reagent containers again to ensure that only the correct reagents are applied.

The dispensing mechanism employs a sensor to detect the level of the fluid in the reagent container, and therefore warns the user when the container is running low. This is important as reagent may have a short useful life when not stored properly, and the reagent is also expensive, therefore there are significant advantages in reducing waste.

The sensor may be attached to the pipette to sense when the pipette reaches the surface of the fluid in the reagent container. This allows the volume of a container to be determined, and a warning maybe sent to the operator is fluid levels drop to a predetermined level. The reagent rack may then be removed from the apparatus, the container replaced, whereupon the scanner will determine whether the correct reagent was replaced by reading the bar code on the reagent container. In this way operator error is reduced.

There are a number of variations described herein, but the apparatus is designed to allow a flexible approach to fluid application, reaction time and temperature. It is therefore not intended that the apparatus be limited to particular examples of potential methodology, as variations in fluid application, cover position and movement.

The protocols that may be applied are varied, and it is possible to apply a different protocol to each sample on a slide in a single rack. Further, it is possible to load a new tray of slides or remove a completed tray of slides while the apparatus is processing another tray of slides.

Without limiting the forgoing, some specific aspects of the invention are recited below, together with a brief description of some advantages of each:

A method of forming a reaction chamber on a slide in a reaction apparatus including:

placing a cover having a cavity on a slide, forming a reaction chamber;

locating the cover and slide in a receptacle of a tray;

providing a receiving portion in the reaction apparatus having a mount for each receptacle in the tray;

loading the tray into a receiving portion of the reaction apparatus, where the receiving portion of the reaction apparatus locates the tray;

releasably holding the cover to the slide; and releasing the tray from the slide and cover.

The above-mentioned method allows a slide and cover to be easily placed into receptacles in a tray. The tray may have a number of receptacles, for example 10 receptacles per tray as shown in the figures of the embodiments disclosed herein. The tray can then be loaded into a receiving portion of the reaction apparatus, so that, for example up to 10 reaction chambers formed from slides and covers, can be placed into the reaction apparatus. As the tray is located by the reaction apparatus upon loading, and the slides and covers are located by the tray, the exact position of up to 10 reaction chambers can be determined easily within the apparatus. Given that slide dimensions vary due to manufacturing inaccuracies, and the covers do not contact the sides of the slides (to eliminate extraneous wicking points), such that the covers can move freely, on top of the slides if not constrained by other means, locating 10 reaction chambers at once can be difficult.

Once the tray is loaded and the slides and covers are fixed in position by the clamps, the tray can be removed. In the present examples the tray is dropped down so that the mounts support the slides and covers. This removes all contact around the edges of the slides except for the wicking posts. Thus it is possible with this arrangement to easily and quickly locate a number of slides and covers without any contact with the sides of the slides. As the covers do not have a positive sealing arrangement, and the reaction chamber is generally full of fluid, this arrangement assists in loading multiple slides without fluid loss thereby minimising bubble formation within the reaction chamber.

An apparatus for loading multiple slides and covers including a tray having a number of receptacles for slides and covers;
a receiving portion for receiving trays;
mounts for each receptacle located in the receiving portions;
a clamp for each mount;
wherein when a tray having slides and covers is loaded into the receiving portion, each clamp holds the cover on the slide to locate the slide, and the tray drops from the slides so each slide is supported by the mount.

Preferably, a draining means is provided.
Preferably the draining means includes a wicking means.
The apparatus above allows slides and covers to be loaded easily by an operator, in batches if required.

A method of undertaking reactions on samples on slides involving multiple steps including:
loading a first holder having at least one slide into a reaction apparatus;
scanning the slide to determine the multiple steps in the reaction to take place on the slide;
determining whether other holders have been loaded into the reaction apparatus;
undertaking the multiple steps required on the at least one slide associated with the first holder;
when the second batch is detected, continue the steps in the reaction associated with the at least one slides in the first holder and then undertaking the at least one steps associated with the slides associated with the second holder.

This is possible in some situations as there are usually gaps where the apparatus used to start or stop reactions, or undertake other tasks (such as the pipette mounted to the robot arm) are not utilised all the time.

If the apparatus are used all the time then the steps of the reaction to take place on the at least one slides associated with the second holder will not commence until the first bath has finished.

An apparatus for performing reactions on slides including a tray having a plurality of receptacles adapted to support and locate slides and associated covers
receiving ports for the trays, the receiving ports having mounts associated with each receptacle of the tray;
a clamping mechanism for clamping the cover and slide in place;
a fluid draining means for draining fluid from the reaction chamber formed between the cover and slide;
fluid receptacles to allow at least one fluid to be placed on the apparatus
fluid dispensing means to dispense fluid onto the slides wherein once the tray is loaded, the slides and cover are clamped and the tray is moved so that the slides and covers are supported on the mounts, fluid may be dispensed onto the slides by the dispensing means, and drained by the draining means.

Preferably, the apparatus includes a locating means for locating and moving the cover with respect to the slide.

Preferably there is a locating means associated with every receptacle in a tray.

Preferably all locating means associated with a particular tray all move at the same time to move the cover with respect to the slide, to facilitate fluid dispensation or draining of all slides on a tray.

An apparatus for applying reagents to sample slides, including:
a plurality of ports for receiving the slides;
a reader for reading identification information on each of the slides; and
a reagent rack for receiving reagent containers which carry reagent to be deposited on the slides; wherein
the slides are provided on trays, which are received in the associated ports such that each tray represents a separate batch of slides, to allow for addition and removal of separate trays, for batch processing during operation of the apparatus.

The batch loading, again, provides substantial flexibility for an operator insofar as testing and scheduling is concerned.

The invention claimed is:
1. An apparatus comprising:
a controller;
a robotic arm;
a dispensing mechanism, mounted on the robotic arm, configured to dispense fluids;
a plurality of individual tray receiving ports disposed under the robotic arm;
a plurality of slide trays, each of the plurality of slide trays comprises a sliding mechanism such that said respective single slide tray is fitted to slide into a respective individual tray receiving port of the plurality of individual tray receiving ports, wherein each slide tray comprises a plurality of slide receiving sections;
a plurality of slides, a single slide of the plurality of slides placed on each slide receiving section of the plurality of slide receiving sections of each slide tray;
a plurality of covers, each cover mounted on a slide of the plurality of slides, wherein each cover comprises a cavity on a side facing the corresponding slide thereby forming a reaction chamber between each slide and its corresponding cover; and
a rack receiving zone comprising a reagent rack which includes a plurality of reagent containers,
wherein the controller comprises non-transient memory including a program to control the dispensing mechanism of the robotic arm to dispense fluid onto a slide of one of the slide trays independently of dispensing fluid onto another slide of another one of the slide trays,
wherein the sliding mechanism is rails that extend along a longitudinal side of the sliding tray, wherein each of the plurality of individual tray receiving ports are housing the respective single slide tray of the plurality of slide trays, wherein the plurality of slide trays are fitted to slide into the respective individual tray receiving ports via the respective rails, wherein the rails are on both sides of each of the plurality of slide trays and slide along the longitudinal sides of the respective tray receiving ports, and wherein, in a fully inserted position of the respective single slide tray into the slide receiving port, the slide tray is not in direct contact with the slides in the slide receiving sections and the slides come in contact and are supported, from underneath, by a plurality of blocks of the respective individual tray receiving port, wherein the plurality of blocks support respective slides of the plurality of slides.

2. The apparatus of claim 1, wherein the cover comprises an arm portion which slides the cover along the top of the slide thereby changing a size of the reaction chamber in response to the sliding of the arm portion.

3. The apparatus of claim 2, wherein each of the slide trays comprises a pair of ramps including slots, and the cover comprises wings which engage the pair of ramps in the slots in response to sliding of the arm portion.

4. The apparatus of claim 3, further comprising:
an actuator which engages a positioning member to move the arm portion to slide the cover over the slide, wherein the actuator is controlled by the controller.

5. The apparatus of claim 3, further comprising:
a clamp which secures the cover to the slide during processing of a sample on the slide.

6. The apparatus of claim 1, wherein each of the tray receiving ports comprises the plurality of blocks corresponding to the plurality of slide receiving sections in the respective slide trays, wherein the plurality of blocks support the plurality of the slides.

7. The apparatus of claim 6, wherein when the respective slide trays are received in the respective tray receiving ports, the plurality of blocks support the plurality of the slides and the respective slide trays are not in direct contact with the plurality of slides.

8. The apparatus of claim 6, further comprising:
a plurality of wicking posts respectively provided for the plurality of the blocks, wherein the plurality of wicking posts further supports the plurality of the slides.

9. The apparatus of claim 8, wherein a block, from among the plurality of the blocks, comprises an upper surface inclined towards a wicking post, from among the plurality of the wicking posts, provided for the block, wherein the upper surface is inclined with respect to a horizontal of the slide tray.

10. The apparatus of claim 1, wherein the controller is programmed to remove and replace the reagent rack with a new reagent rack without interrupting operations of the robotic arm during a process run in which the robotic arm is in use.

11. The apparatus of claim 1, wherein the dispensing mechanism comprises a fluid conduit which dispenses fluids,
wherein a plurality of samples for undergoing reactions are respectively placed on the plurality of slides, and in response to at least one of the tray receiving ports receiving the respective slide trays, the controller is programmed to scan the plurality of slides to determine a reaction to be performed at each individual slide.

12. The apparatus of claim 11, wherein based on the determined reaction, the controller is programmed to perform a dispensing operation by determining a reagent required to perform the reaction at the slide, and determine whether at least one of the plurality of reagent containers includes the determined reagent.

13. The apparatus of claim 12, wherein in response to determining that at least one of the plurality of reagent containers includes the determined reagent, the controller is programmed to continue the dispensing operation by controlling the robotic arm (i) to move the dispensing mechanism to the at least one reagent container to withdraw the determined reagent from the at least one reagent container into the fluid conduit, (ii) to move the dispensing mechanism to the slide, and (iii) to dispense the withdrawn reagent from the fluid conduit into the reaction chamber.

14. The apparatus of claim 13, wherein the controller is programmed to repeat the dispensing operation for each individual slide on the respective slide trays to process the slides as a batch.

15. The apparatus of claim 14, further comprising:
a washing station comprising:
a receptacle for receiving the fluid conduit, wherein the controller is programmed to pump cleaning fluid from a bulk reagent container into the receptacle to clean the fluid conduit between performances of the dispensing operation for each individual slide.

16. The apparatus of claim 12, further comprising:
a bulk reagent container section; and
a plurality of bulk reagent containers stored in the bulk reagent container section,
wherein in response to determining that at least one of the plurality of reagent containers does not include the determined reagent, the controller is further programmed to continue the dispensing operation by controlling the robotic arm (i) to determine whether at least one of the bulk reagent containers includes the determined reagent and (ii) to refill, in response to determining that at least one of the bulk reagent containers includes the determined reagent, the at least one reagent container in the reagent rack with the reagent included in the at least one bulk reagent container, (iii) to move the dispensing mechanism to the at least one reagent container to withdraw the determined reagent from the at least one reagent container into the fluid conduit, (iv) to move the dispensing mechanism to the slide, and (v) to dispense the withdrawn reagent from the fluid conduit into the reaction chamber.

17. The apparatus of claim 1, wherein the rails of each of the plurality of slide trays are positioned below the plurality of slide receiving sections and wherein the rails are on both sides of the plurality of slide trays.

18. The apparatus of claim 1, further comprising: a locator arm which moves the corresponding cover relative to the respective slide from among the slides via a locator engaging element,
wherein the locator arm is engaged by a bracket from among a plurality of brackets corresponding to the plurality of slide receiving sections, and
wherein each of the plurality of individual receiving ports operate independently of each other.

19. An apparatus comprising:
a controller;
a robotic arm;
a dispensing mechanism, mounted on the robotic arm, configured to dispense fluids;

a plurality of individual tray receiving ports disposed under the robotic arm;

a plurality of slide trays, each of the plurality of slide trays comprises a sliding mechanism such that said respective single slide tray is fitted to slide into a respective individual tray receiving port of the plurality of individual tray receiving ports, wherein each slide tray comprises a plurality of slide receiving sections;

a plurality of slides, a single slide of the plurality of slides placed on each slide receiving section of the plurality of slide receiving sections of each slide tray;

a plurality of covers, each cover mounted on a slide of the plurality of slides, wherein each cover comprises a cavity on a side facing the corresponding slide thereby forming a reaction chamber between each slide and its corresponding cover; and a rack receiving zone comprising a reagent rack which includes a plurality of reagent containers, wherein the controller comprises non-transient memory including a program to control the dispensing mechanism of the robotic arm to dispense fluid onto a slide of one of the slide trays independently of dispensing fluid onto another slide of another one of the slide trays, wherein the sliding mechanism is rails that extend along a longitudinal side of the sliding tray, wherein each of the plurality of individual tray receiving ports are housing the respective single slide tray of the plurality of slide trays, wherein each of the tray receiving ports comprises a plurality of blocks corresponding to the plurality of slide receiving sections in the respective slide trays, wherein the plurality of blocks support the plurality of the slides, wherein the slides come in contact and are supported, from underneath, by the plurality of blocks of the respective individual tray receiving port, and wherein when the respective slide trays are received in the respective tray receiving ports, the plurality of blocks support the plurality of the slides and the respective slide trays are not in direct contact with respective slides of the plurality of slides.

20. The apparatus of claim 19, wherein the cover comprises an arm portion which slides the cover along the top of the slide thereby changing a size of the reaction chamber in response to the sliding of the arm portion.

21. The apparatus of claim 20, wherein each of the slide trays comprises a pair of ramps including slots, and the cover comprises wings which engage the pair of ramps in the slots in response to sliding of the arm portion.

* * * * *